(12) United States Patent
Walczak et al.

(10) Patent No.: US 10,653,678 B2
(45) Date of Patent: May 19, 2020

(54) METHODS OF TREATMENT FOR CHOLESTATIC AND FIBROTIC DISEASES

(71) Applicant: Genfit, Loos (FR)

(72) Inventors: Robert Walczak, Lille (FR); Corinne Foucart, La Madeleine (FR); Philippe Delataille, Ronchin (FR)

(73) Assignee: GENFIT, Loos (FR)

( * ) Notice: Subject to any disclaimer, the term of this patent is extended or adjusted under 35 U.S.C. 154(b) by 49 days.

(21) Appl. No.: 15/958,713

(22) Filed: Apr. 20, 2018

(65) Prior Publication Data

US 2018/0280358 A1  Oct. 4, 2018

Related U.S. Application Data

(63) Continuation-in-part of application No. 15/457,402, filed on Mar. 13, 2017, now abandoned.

(30) Foreign Application Priority Data

Apr. 11, 2016 (EP) .................................. 16305427

(51) Int. Cl.
*A61K 31/426* (2006.01)
*A61P 1/16* (2006.01)
*A61K 31/40* (2006.01)

(52) U.S. Cl.
CPC ............ *A61K 31/426* (2013.01); *A61P 1/16* (2018.01); *A61K 31/40* (2013.01); *A61K 2300/00* (2013.01)

(58) Field of Classification Search
CPC .............................. A61K 31/426; A61K 31/40
USPC .................................................. 514/371, 423
See application file for complete search history.

(56) References Cited

U.S. PATENT DOCUMENTS 9,370,528 B2 * 6/2016 Schentag ............... A61K 45/06
2011/0244027 A1  10/2011 Chu et al.

FOREIGN PATENT DOCUMENTS

| WO | 2009023509 | 2/2009 |
|---|---|---|
| WO | 2009039246 | 3/2009 |
| WO | 2009039248 | 3/2009 |
| WO | 2010121128 | 10/2010 |
| WO | 2011060408 | 5/2011 |
| WO | 2011140190 | 11/2011 |
| WO | 2011140296 | 11/2011 |
| WO | 2012013716 | 2/2012 |
| WO | 2012158552 | 5/2012 |
| WO | 2012118712 | 9/2012 |
| WO | 2014036528 | 3/2014 |

OTHER PUBLICATIONS

González-Casas, et al, [Chronic C hepatitis genotype 4], Med Clin (Barc), 2011, 137(1), 31-5; Abstract.
Shehab HM et al, Nitazoxanide plus pegylated interferon and ribavirin in the treatment of genotype 4 chronic hepatitis C, a randomized controlled trial, Liver Int, 2013, 34, (2), 259-65.

* cited by examiner

*Primary Examiner* — Raymond J Henley, III
(74) *Attorney, Agent, or Firm* — Leason Ellis LLP

(57) ABSTRACT

The present invention relates to synergistic combination of active ingredients for use in the treatment of fibrotic diseases.

6 Claims, 13 Drawing Sheets

METHODS OF TREATMENT FOR CHOLESTATIC AND FIBROTIC DISEASES

CROSS-REFERENCE TO RELATED APPLICATIONS

Figure 1:
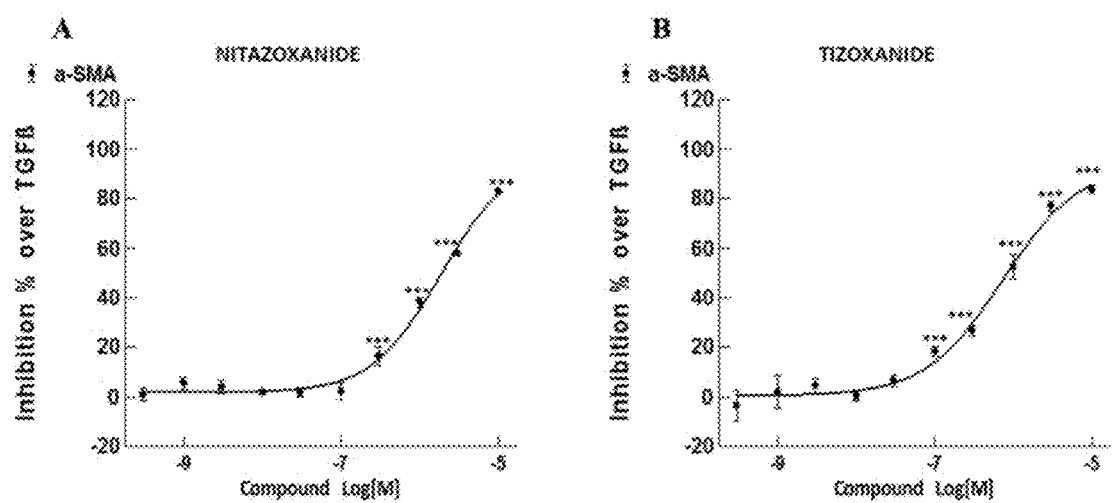

The present application is a continuation-in-part application of U.S. patent application Ser. No. 15/457,402 (filed on Mar. 13, 2017) which is abandoned and claims priority to European Patent Application No. EP16305427.3 (filed on Apr. 11, 2016), each of which is incorporated herein by reference in its entirety.

TECHNICAL FIELD

The present invention relates to the field of medicine, in particular to the treatment of cholestatic or fibrotic diseases.

BACKGROUND

Abnormal and exaggerated deposition of extracellular matrix is the hallmark of all fibrotic diseases, including liver, pulmonary, kidney or cardiac fibrosis. The spectrum of affected organs, the progressive nature of the fibrotic process, the large number of affected persons, and the absence of effective treatment pose an enormous challenge when treating fibrotic diseases.

In an attempt to propose new therapeutic strategies for the treatment of fibrotic diseases, the inventors found that 2-[(5-nitro-1,3-thiazol-2-yl)carbamoyl]phenyl]ethanoate (Nitazoxanide—NTZ), a synthetic antiprotozoal agent or its deuterated derivatives or its active metabolite 2-hydroxy-N-(5-nitro-2-thiazolyl)benzamide (Tizoxanide, known as TZ) in combination with statins show synergistic antifibrotic activities. Moreover, the evaluation of NTZ combined to a statin in a liver injury model revealed its capacity to reduce circulating bile acid concentration, thus reflecting the synergistic potential of this combination to treat both cholestatic (such as PBC and PSC) and fibrotic diseases.

NTZ, first described in 1975 (Rossignol and Cavier, 1975), was shown to be highly effective against anaerobic protozoa, helminths, and a wide spectrum of microbes including both anaerobic and aerobic bacteria (Rossignol and Maisonneuve, 1984 Dubreuil, Houcke et al., 1996; Megraudd, Occhialini et al., 1998; Fox and Saravolatz, 2005; Pankuch and Appelbaum, 2006; Finegold, Molitoris et al., 2009). It was first studied in humans for the treatment of intestinal cestodes (Rossignol and Maisonneuve, 1984) and it is now licensed in the United States (Annie®, Romark laboratories) for the treatment of diarrhea caused by the protozoan parasites *Crystosporidium parvum* and *Giardia intestinalis*. NTZ has also been widely commercialized in Latin America and in India where it is indicated for treating a broad spectrum of intestinal parasitic infections (Hemphill, Mueller et al., 2006). The proposed mechanism of action by which NTZ exerts its antiparasitic activity is through the inhibition of pyruvate:ferredoxin oxidoreductase (PFOR) enzyme-dependent electron transfer reactions that are essential for anaerobic metabolism (Hoffman, Sisson et al., 2007). NTZ also exhibited activity against *Mycobacterium tuberculosis*, which does not possess a homolog of PFOR, thus suggesting an alternative mechanism of action. Indeed, the authors showed that NTZ can also act as an uncoupler disrupting membrane potential and intra-organism pH nomeostasis. (de Carvalho, Darby et al., 2011).

The pharmacological effects of NTZ are not restricted to its antiparasitic or antibacterial activities and in recent years, several studies revealed that NTZ can also confer antiviral activity (Di Santo and Ehrisman, 2014; Rossignol, 2014). NTZ interferes with the viral replication by diverse ways including a blockade in the maturation of hernagglutinin (influenza) or VP7 (rotavirus) proteins, or the activation of the protein PKR involved in the innate immune response (for a review, see (Rossignol, 2014)). NTZ was also shown to have broad anticancer properties by interfering with crucial metabolic and prodeath signaling pathways (Di Santo and Ehrisman, 2014).

Statins (3-hydroxy-3-methylglutaryl-coenzyme A reductase inhibitors) are commonly prescribed as medications for the treatment of hypercholesterolemia and for the prevention of cardiovascular disease.

There are currently 7 unique prescribed statins that include pravastatin, simvastatin, and lovastatin (which are naturally-derived from fungal fermentation) and a second group of chemically synthesized statins composed of fluvastatin, atorvastatin, rosuvasatin and pitavastatin. Although all statins contain a dihydroxy-heptanoic acid HMG-CoA like moiety, which competes for binding to HMG-CoA reductase, each statin is unique and exhibits significant differences in chemical structure, potency (ex. $IC_{50}$ for HMG-CoA reductase inhibition), tissue penetration and retention, half-fife, metabolism and elimination, drug-drug interactions, and safety. The mechanisms involved in the beneficial effects of statins on the prevention of cardiovascular disease have been largely attributed to the ability of these agents to inhibit cholesterol biosynthesis. Owing to the fact that 60-70% of serum cholesterol is derived from hepatic biosynthesis and that HMG-CoA reductase is the crucial, rate-limiting enzyme in the cholesterol biosynthetic pathway, it is not surprising that inhibition of this enzyme results in a dramatic reduction in circulating LDL-Cholesterol. Moreover, reduction of LDL-cholesterol leads to upregulation of hepatic LDL receptors and increase of LDL clearance. Both clinical and experimental data suggest that the sum of benefits from statin therapy may extend well beyond their favorable effects on serum cholesterol levels. These cholesterol-independent effects, described as pleiotropic effects of statins, are related to the reduced formation of isoprenoids. Indeed, inhibition of HMG-CoA reductase results not only in deprivation of intracellular mevalonate but also several downstream isoprenoid derivatives including farnesyl pyrophosphate (FPP) and geranylgeranylpyrophosphate(GGPP). Both FPP and GGPP are required for posttranslational prenylation of a number of proteins (approximately 2% of total cellular proteins, (Wang, Liu et al., 2008)). Protein isoprenylation enables proper subcellular localization and trafficking of intracellular molecules. For example, non-isoprenylated GTPases remain cytosolic whereas isoprenylated GTPases harbour a FPP or GGPP lipid attachment that permits insertion and anchorage into the cell membrane, and subsequently participate in signal transduction. Therefore, inhibiting isoprenylation results in the inactivation of the small GTPases (ex Rho, Ras, Rac and Cdc42) which are essential in many cellular events (intracellular signal transduction, cellular proliferation, inflammation, motility, (for a review see (McFarlane, Muniyappa et al., 2002; Zhou and Liao, 2009; Yeganeh, Wiecher et al., 2014; Kavalipati, Shah et al., 2015)). Since it has been demonstrated that the Rho GTPase and its target protein Rock are involved in the activation/differentiation of fibroblasts into myofibroblasts (Ji, Tang et al., 2014), a key event in the fibrotic process, several studies were conducted with statins to evaluate their antifibrotic properties in different pathological models. Simvastatin was shown to reduce the expression of fibrotic markers in both human and rat HSC and to confer antifibrotic properties in various animal models of fibrosis (Rombouts, Kisanga et al., 2003; Watts, Sampson et al., 2005; Wang, Zhao et al., 2013, Marrone, Maeso-Diaz et al., 2015). As well, Pitavastatin (Miyaki, Nojiri et al., 2011) and Fluvastatin (Chong, Hsu et al., 2015) were able to reduce fibrosis in the CDAA diet-induced NAFLD/NASH model. These beneficial effects of statins are not restricted to liver fibrosis. Indeed, it was demonstrated that Atorvastatin was significantly potent against bleomycin-induced lung fibrosis (Zhu, Ma et at, 2013) while Simvastatin was shown to inhibit expression of fibrotic markers in fibroblasts derived from human fibrotic lung. (Watts, Sampson et al., 2005).

In this invention, using a phenotypic screening assay to identify potential antifibrotic agents, it was discovered that NTZ or its deuterated derivatives or its active metabolite TZ, in combination with a statin, interferes, in an additive or synergistic manner, with the activation of myofibroblasts. This effect was totally unexpected in view of the properties previously reported for these molecules. Combination of NTZ or its deuterated derivatives or TZ with a specific statin appears as a potent therapeutic strategy for diverse types of fibrotic diseases. Moreover, the evaluation of NTZ or derivatives thereof in combination with a specific statin revealed an unexpected synergistic capacity to reduce circulating bile acid concentration, thus reflecting its potential to treat both cholestatic diseases (such as PBC and PSC) and fibrotic diseases.

SUMMARY OF INVENTION

The present invention relates to a synergistic combination comprising (i) [2-[(5-nitro-1,3-thiazol-2-yl)carbamoyl]phenyl]ethanoate (NTZ), a deuterated derivative of NTZ (NTZ-D), 2-hydroxy-N-(5-nitro-2-thiazolyl)benzamide (TZ), or Tizoxanide glucuronide (TZG) and (ii) at least one statin. This combination is useful in a method for the treatment of a cholestatic or fibrotic disease.

Therefore, the present invention relates to a synergistic combination of
(i) NTZ, NTZ-D, TZ or TZG, or a pharmaceutically acceptable salt of NTZ, NTZ-D, TZ or TZG.
(ii) a statin.

The combination of the invention may be in the form of a pharmaceutical composition or of a kit-of-parts.

Furthermore, the components of the synergistic combination the invention may be administered simultaneously, sequentially and separately.

In a particular embodiment, component (i) of the synergistic combination is NTZ or a pharmaceutically acceptable salt thereof.

In a particular embodiment of the invention, said at least one statin is selected in the group consisting of mevastatin, cerivastatin, pitavastatin, fluvastatin, simvastatin, atorvastatin, lovastatin, rosuvastatin, and pravastatin. In another particular embodiment, the statin is selected in the group consisting of pitavastatin, fluvastatin, simvastatin and atorvastatin. In another particular embodiment, the statin is selected in the group consisting of pitavastatin, fluvastatin and simvastatin.

Furthermore, the synergistic combination of the invention may further comprise at least one therapeutically active agent with known antifibrotic activity selected from pirfenidone or receptor tyrosine kinase inhibitors (RTKIs) such as Nintedanib, Sorafenib and other RTKIs, or angiotensin II (AT1) receptor blockers, or CTGF inhibitor, or any antifibrotic compound susceptible to interfere with the TGFβ and BMP-activated pathways including activators of the latent TGFβ complex such as MMP2, MMP9, THBS1 or cell-surface integrins, TGFβ receptors type I (TGFBRI) or type II (TGFBRII) and their ligands such as TGFβ, Activin, inhibin, Nodal, anti-Mülleriam hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process, or canonical and non-canonical Hedgehog signaling pathways including Hh ligands or target genes, or any members of the WNT, or Notch pathways which are susceptible to influence TGFβ signaling.

Alternatively, the synergistic combination according to the invention may further comprise at least one therapeutically active agent selected from JAK/STAT inhibitors and other anti-inflammatory agents and/or immunosuppressant agents. For example, the therapeutically active agent may be selected from glucocorticoids, NSAIDS, cyclophosphamide, nitrosoureas, folic acid analogs, purine analogs, pyrimidine analogs, methotrexate, azathioprine, mercaptopurine, ciclosporin, myriocin, tacrolimus, sirolimus, mycophenolic acid derivatives, fingolimod and other sphingosine-1-phosphate receptor modulators, monoclonal and/or polyclonal antibodies against such targets as proinflammatory cytokines and proinflammatory cytokine receptors, T-cell receptor and integrins.

The present invention also relates to the synergistic combination according to the invention, for use as a medicament.

Furthermore, the invention relates to the synergistic combination described herein, for use in a method for treating a fibrotic disorder. In a particular embodiment, the fibrotic disorder is selected in the group consisting of liver, gut, kidney, skin, epidermis, endodermis, muscle, tendon, cartilage, heart, pancreas, lung, uterus, nervous system, testis, penis, ovary, adrenal gland, artery, vein, colon, intestine (e.g. small intestine), biliary tract, soft tissue (e.g. mediastinum or retroperitoneum), bone marrow, joint, eye and stomach fibrosis. In a further particular embodiment, the fibrotic disorder is selected in the group consisting of liver, kidney, skin, epidermis, endodermis, muscle, tendon, cartilage, heart, pancreas, lung, uterus, nervous system, testis, ovary, adrenal gland, artery, vein, colon, intestine (e.g. small intestine), biliary tract, soft tissue (e.g. mediastinum or retroperitoneum), bone marrow, joint and stomach fibrosis. In a further particular embodiment, the fibrotic disorder is selected in the group consisting of liver, gut, lung, heart, kidney, muscle, skin, soft tissue, bone marrow, intestinal, and joint fibrosis. In yet another embodiment the fibrotic disorder is selected in the group consisting of non-alcoholic steatohepatitis (NASH), pulmonary fibrosis, idiopathic pulmonary fibrosis, skin fibrosis, eye fibrosis (such as capsular fibrosis), endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, lung fibrosis consecutive to chronic inflammatory airway disease (COPD, asthma, emphysema, smoker's lung, tuberculosis), alcohol or drug-induced liver fibrosis, liver cirrhosis, infection-induced liver fibrosis, radiation or chemotherapeutic-induced fibrosis, nephrogenic systemic fibrosis, Crohn's disease, ulcerative colitis, keloid, old myocardial infarction, scleroderma/systemic sclerosis, arthrofibrosis, some forms of adhesive capsulitis, chronic fibrosing cholangiopathies such as Primary Sclerosing Cholangitis (PSC). Primary Biliary Cholangitis (PBC), biliary atresia, familial intrahepatic cholestasis type 3 (PFIC3), peri-implantational fibrosis and asbestosis.

According to a particular embodiment of the invention, the cholestesatic disease is selected in the group consisting of primary biliary cholangitis (PBC), primary sclerosing cholangitis (PSC), Intrahepatic Cholestasis of Pregnancy, Progressive Familial Intrahepatic Cholestasis, Biliary atresia, Cholelithiasis, infectious Cholangitis, Cholangitis associated with Langerhans cell histiocytosis. Alagille syndrome, Nonsyndromic ductal paucity. Drug-induced cholestasis, and Total parenteral nutrition-associated cholestasis. In a particular embodiment, the cholestatic disease is PBC.

According to a particular embodiment, in each aspects and embodiments described herein, NTZ, NTZ-D or TZ, or a pharmaceutically acceptable salt of NTZ; NTZ-D or TZ is used.

DESCRIPTION OF THE FIGURES AND TABLES

Abbreviations Used in the Figures, in the Tables, and in the Text:
α-SMA: alpha Smooth Muscle Actin
ATORVA: Atorvastatin
BDL: Bile Duct Ligation
BMP: Bone Morphogenetic Protein
cDNA: Complementary Deoxyribonucleotide acid
COL1A1: Collagen, type 1, Alpha 1
CDAk Choline-Deficient L-Amino Acid
CDAAc: Choline-Deficient L-Amino Acid-defined diet suppler en with cholesterol
CHOL: cholesterol
CSAA: Choline Supplemented L-Amino Acid-defined
DDC: 3,5-diethoxycarbonyl-1,4-dihydrocolhdine
DMSO: Dimethyl sulfoxide
DTT: Dithiothreitol
ELISA: Enzyme-Linked immunosorbent Assay
EMT: Epithelial-mesenchymal transition
EOB: Excess Over Bliss
FBS: Fetal Bovine Serum
FDA: Food and Drug Administration
FLUVA: Fluvastatin
FPP: Farnesyl Pyrophosphate
GDF: Growth Differentiation Factors
Hh: Hedgehog
GGPP: Geranylgeranipyrophosphate
HMG-CoA: 3-hydroxy-3-methylgiutarykroenzyme A
hHSC: Human Hepatic Stellate Cells
HSC: Hepatic Stellate Celis
$IC_{50}$: Half maximal Inhibitory Concentration
InMyoFib: intestinal Myofibroblasts
MMP2: Matrix Metallopeptidase 2
MMP9: Matrix Metallopeptidase 9
µl: microliter
LDL: Low Density Lipoprotein
LOVA: Lovastatin
NHLF: Normal Human Lung Fibroblasts
NTZ: Nitazoxanide
PBC: Primary Mary Cholangitis
PBS: Phosphate Buffer Saline
PITA: Pitavastatin
PSC: Primary Sclerosing Cholangitis
qPCR: Quantitative Polymerase Chain Reaction
pMol: picomoles PRAVA: Pravastatin
rhFGF: recombinant human basic Fibroblast Growth Factor
ROSU: Rosuvastatin
RNA: Ribonucleic Add
RT: Reverse Transcriptase
SIMVA: Simvastatin
SmBM: Smooth Muscle cell Basal Medium
SteCGS: Stellate Cell Growth Supplement
STeCIVI: Stellate Cell Medium
TBA: Total Bile Acids
TGFβ1: Tumor Growth Factor beta 1
TGFBRI: TGFb type I receptor
TGFBRII: TGFb type II receptor
THBS1: Thrombospondine 1
TMB: Tetramethylbenzidine
TZ: Tizoxanide
TZG: Tizoxanide glucuronide FIG. 1: Nitazoxanide and its Metabolite Tizoxanide Inhibit TGFβ1-Induced Expression of α-SMA Protein in Human HSC Serum-deprived HSC were preincubated for 1 hour with NTZ (A) or TZ (B) before the activation with the profibrogenic cytokine TGFβ1(1 ng/ml). After 48 hours of incubation, the expression of α-SMA was measured by ELISA. The obtained values were transformed into percentage inhibition over TGFβ1 control. Data are presented as mean (triplicates)±standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus TGFβ1 1 ng/mL group)]. The curve fitting and the calculation of half maximal inhibitory concentration ($IC_{50}$) were performed with XLFit software 5.3.1.3.

Figure 2:
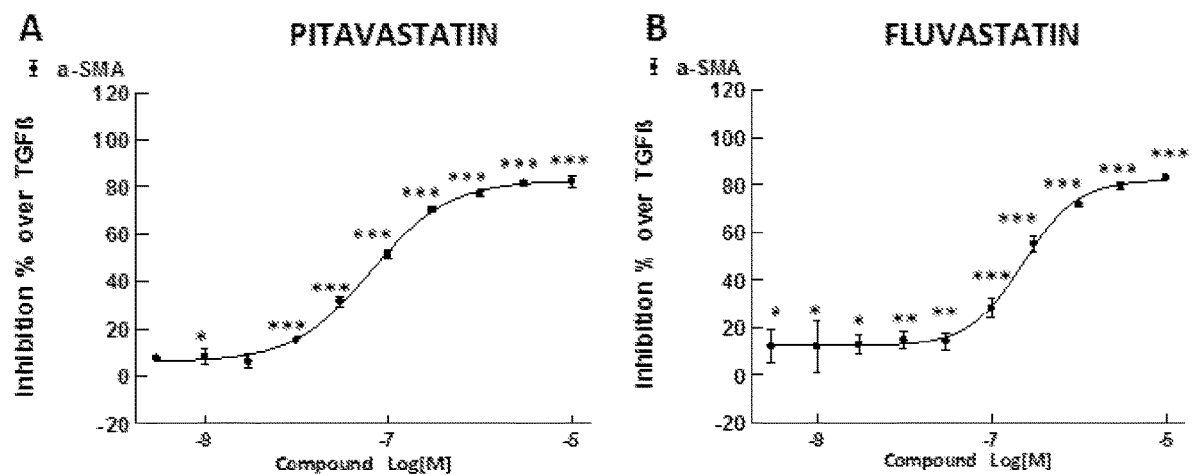
Figure 2:
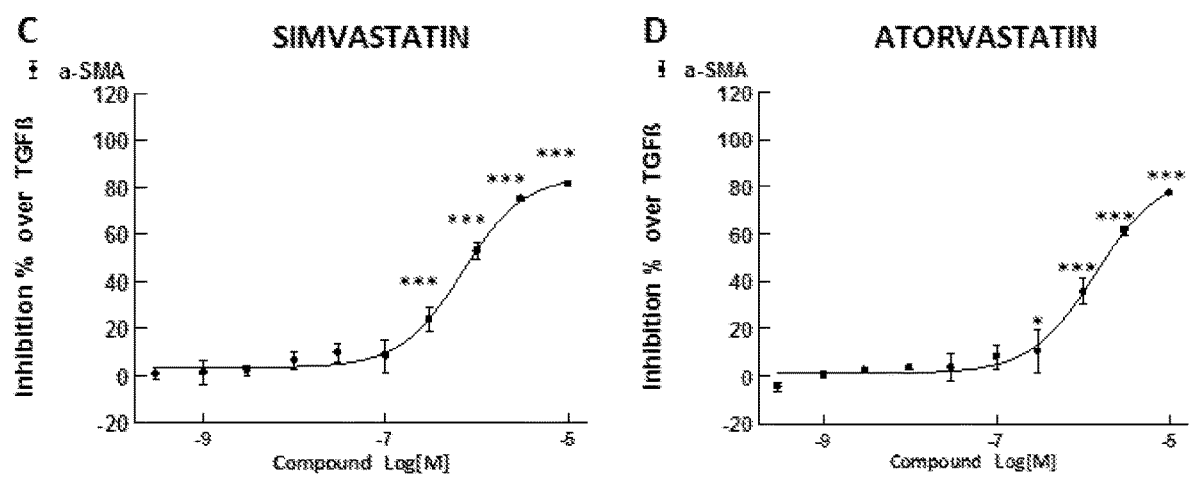
Figure 2:
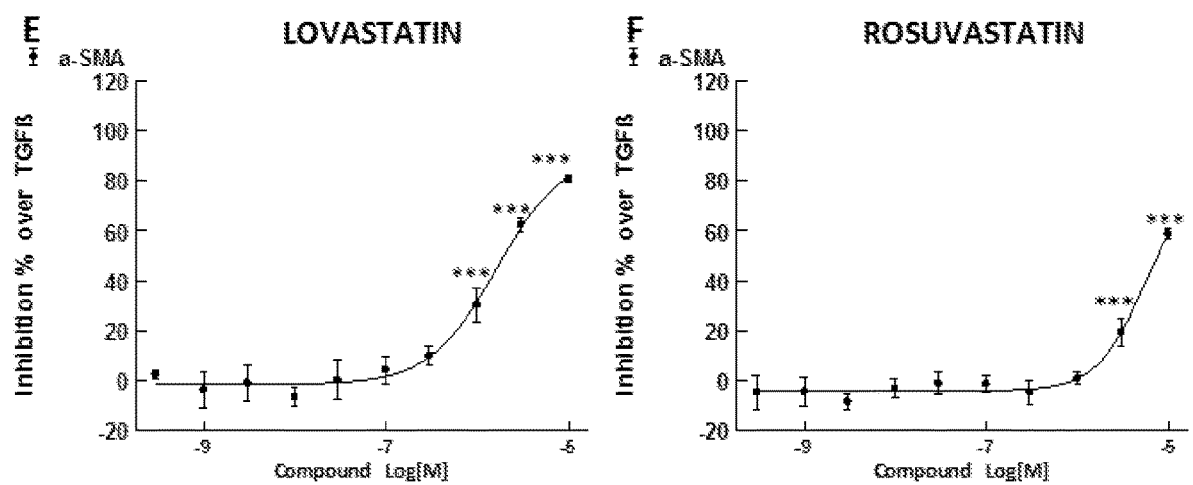
Figure 2:
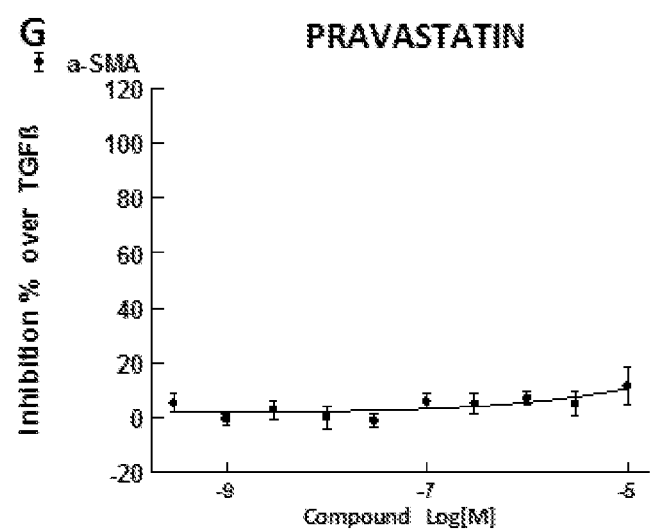

FIG. 2: Differential Antifibrotic Effect of Statin Drugs, in TGFβ-Induced hHSC

Serum-deprived hHSC were preincubated for 1 hour with Pitavastatin (A), Fluvastatin (B), Simvastatin (C), Atorvastatin (D), Lovastatin (E), Rosuvastatin (F) and Pravastatin (G) before the activation with the profibrogenic cytokine TGFβ1 (1 ng/ml). After 48 hours of incubation, the expression of α-SMA was measured by ELISA. The obtained values were transformed into percentage inhibition over TGFβ1 control. Data are presented as mean (triplicates) ±standard deviation (SD). Statistical analyses were performed by one-way ANOVA followed by Bonferroni post-hoc tests, using Sigma Plot 11.0 software. [*: $p<0.05$; : $p<0.01$; *: $p<0.001$ (comparison versus TGFβ1 1 ng/mL group)]. The curve fitting and the calculation of half maximal inhibitory concentration ($IC_{50}$) were performed with XLFit software 5.3.1.3.

Figure 3:
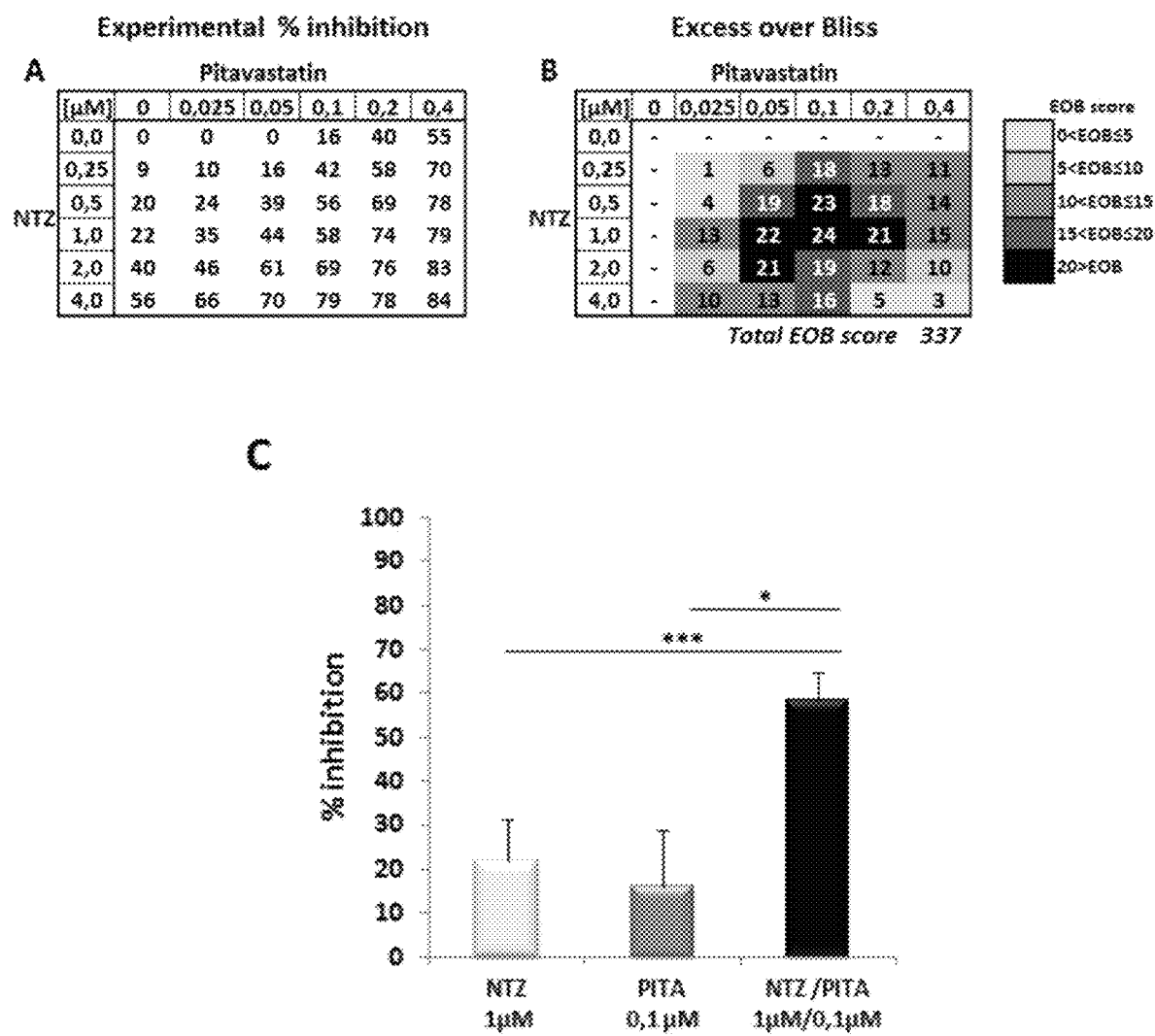

FIG. 3: Combination of NTZ and Pitavastatin Synergistically α-SMA in TGFβ1-Induced hHSC Combinations were tested in a dose-response matrix format and analyzed according to the excess over Bliss (EOB) additivism model. Dilution series of NTZ (column) and Pitavastatin (row) were prepared, including their respective DMSO controls. The resulting mixes were added to serum-deprived HSC, 1 hour prior to the activation with the profibrogenic cytokine TGFβ1 (1 ng/ml). (A) Percentage of α-SMA inhibition over the TGFβ1 control for all combination pairs. Data are presented as mean of quadruplicates. (B) EOB scores were calculated as described in Materials and Methods. Any compound pair with positive EOB values was considered synergistic (colored from light grey to black). (C) Data values derived from a synergistic combination pair were plotted in a bar graph representation. Data are presented as mean (quadruplicates)±standard deviation (SD).

Statistical analyses between single agent vs product combination were performed by student t-test or Mann-Whitney Rank Sum Test using Sigma Plot 11.0 software, [*: $p<0.05$; : $p<0.01$; *: $p<0.001$].

Figure 4:
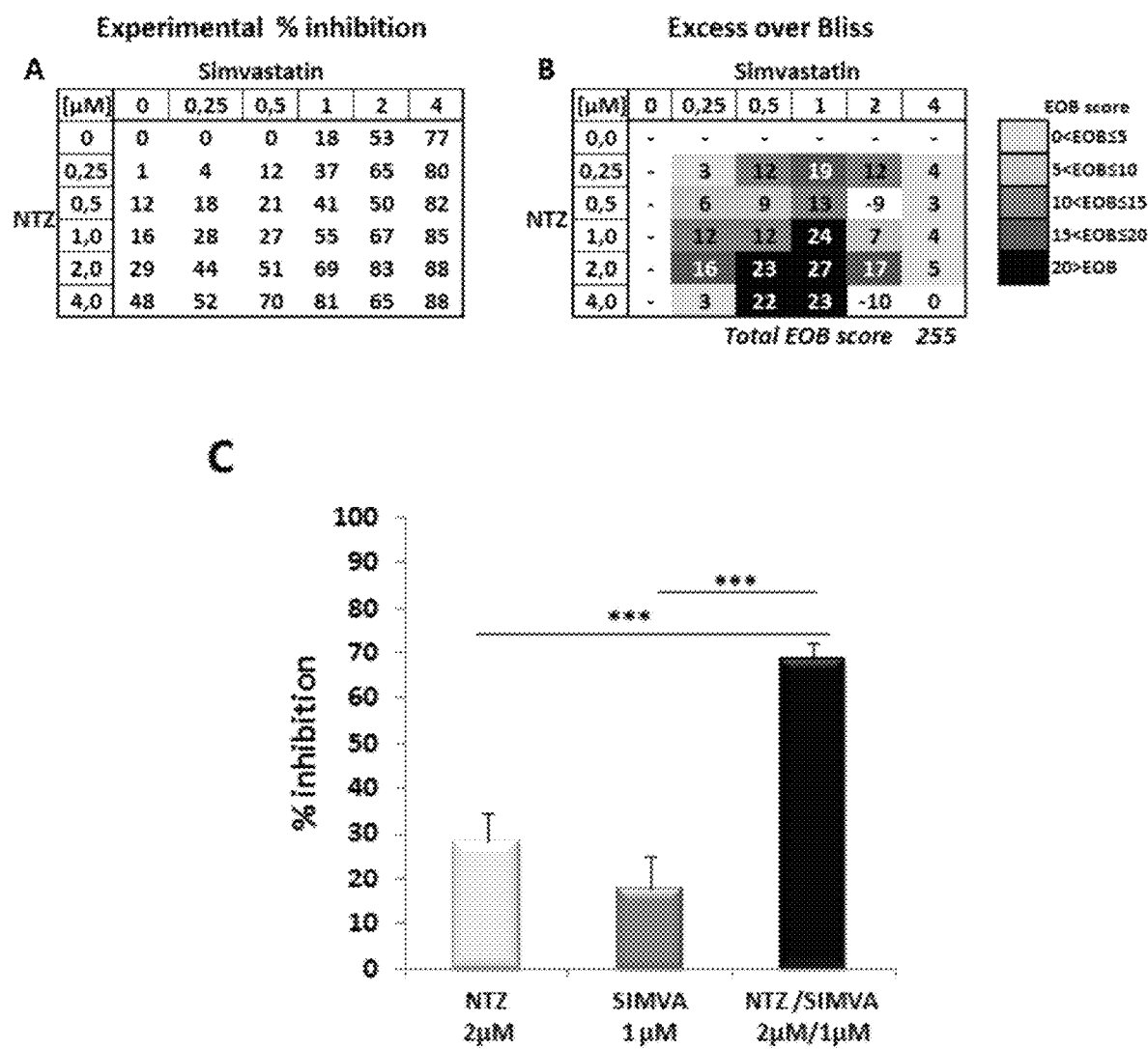

FIG. 4: Combination of NTZ and Simvastatin Synergistically Inhibits α-SMA in TGRβ-Induced hHSC Combinations were tested in a dose-response matrix format and analyzed according to the excess over Bliss (EOB) additivism model. Dilution series of NTZ (column) and Simvastatin (row) were prepared, including their respective DMSO controls. The resulting mixes were added to serum-deprived HSC 1 hour prior to the activation with the profibrogenic cytokine TGFβ1 (1 ng/ml). (A) Percentage of β-SMA inhibition over the TGFβ1 control for all combinations. (B) EOB scores were calculated as described in Materials and Methods. Any compound pair with positive EOB values was considered synergistic (colored from light grey to black). (C) Data values derived from a synergistic combination pair were plotted in a bar graph representation. Data are presented as mean (quadruplicates)±standard deviation (SD). Statistical analyses between single agent vs product combination were performed by student t-test or Mann-Whitney Rank Sum Test using Sigma Plot 11.0 software, [*: $p<0.05$; : $p<0.01$; *: $p<0.001$].

Figure 5:
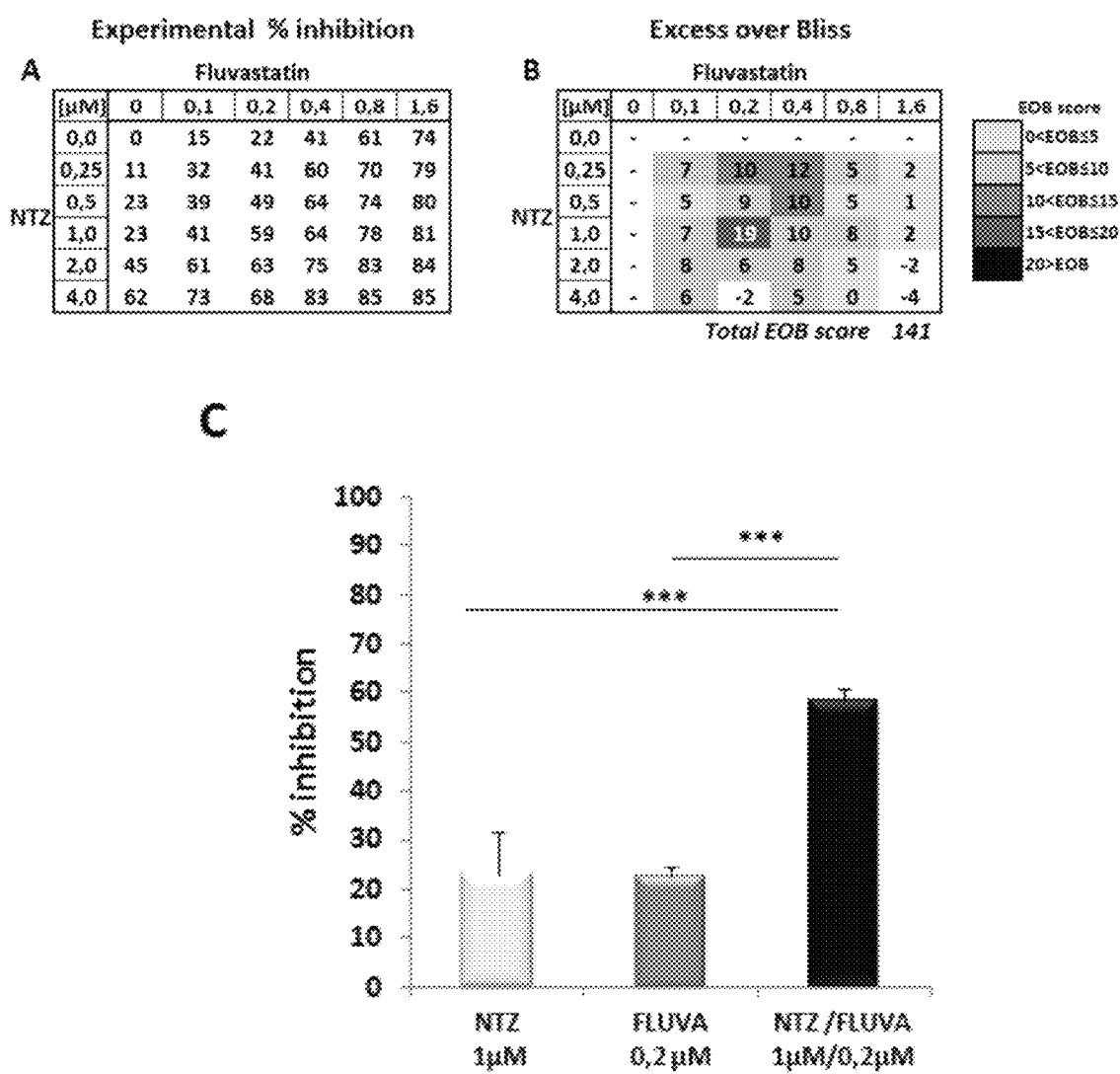

FIG. 5: Combination of NTZ and Fluvastatin Synergistically Inhibits α-SMA in TGFβ-Induced hHSC Combinations were tested in a dose-response matrix format and analyzed according to the excess over Bliss additivism model. Dilution series of NTZ (column) and Fluvastatin (row) were prepared, including their respective DMSO controls. The resulting mixes were added to serum-deprived HSC, 1 hour prior to the activation with the profibrogenic cytokine TGFβ1 (1 ng/ml). (A) Percentage of α-SMA inhibition over the TGFβ1 control for all combinations. (B) Excess over Bliss (EOB) scores were calculated as described in Materials and Methods. Any compound pair with positive EOB values is considered synergistic (colored from light grey to black), (C) Data values derived from a synergistic combination pair were plotted in a bar graph representation. Data are presented as mean (quadruplicates)±standard deviation (SD). Statistical analyses between single agent vs product combination were performed by student t-test or Mann-Whitney Rank Sum Test using Sigma Plot 11.0 software, [*: $p<0.05$; : $p<0.01$; *: $p<0.001$].

Figure 6:
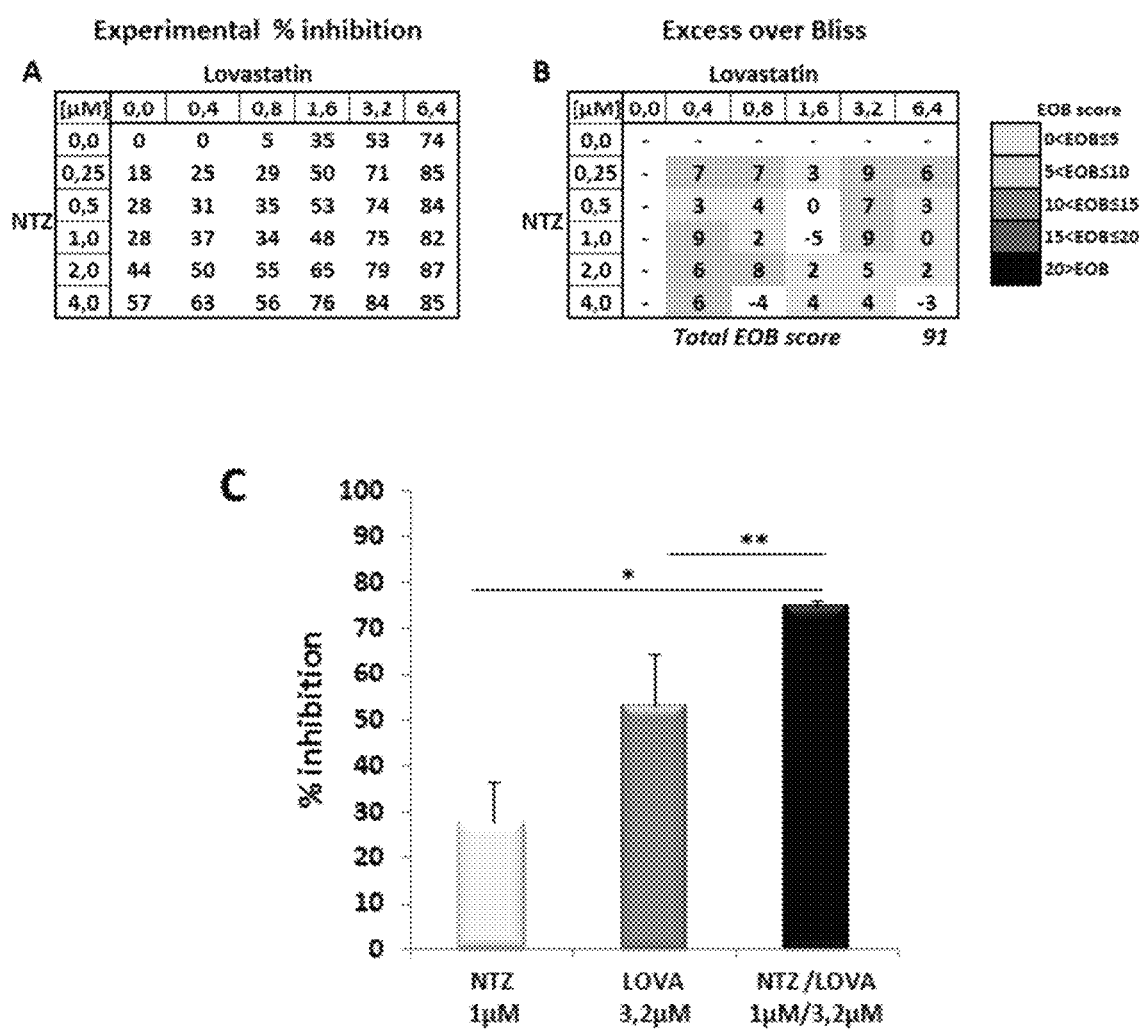

FIG. 6: Combination of NTZ and Lovastatin Synergistically Inhibit α-SMA in TGFβ-Induced hHSC Combinations were tested in a dose-response matrix format and analyzed, to the excess over Bliss additivism model. Dilution series of NTZ (column) and Lovastatin (row) were prepared, including their respective DMSO controls. The resulting mixes were added to serum-deprived HSC 1 hour prior to the activation with the profibrogenic cytokine TGFβ1 (1 ng/ml). (A) Percentage inhibition of α-SMA over the TGFβ1 control for all combinations, (B) Excess over Bliss (EOB) scores were calculated as described in Materials and Methods. Any compound pair with positive EOB values is considered synergistic (colored from light grey to black. An example of a synergistic pair is illustrated in a (C) Data values derived from a synergistic combination pair were plotted in a bar graph representation. Data are presented as mean (quadruplicates)±standard deviation (SD). Statistical analyses between single agent vs product combination were performed by student t-test or Mann-Whitney Rank Sum Test using Sigma Plot 11.0 software. [*: $p<0.05$; : $p<0.01$; *: $p<0.001$].

Figure 7:
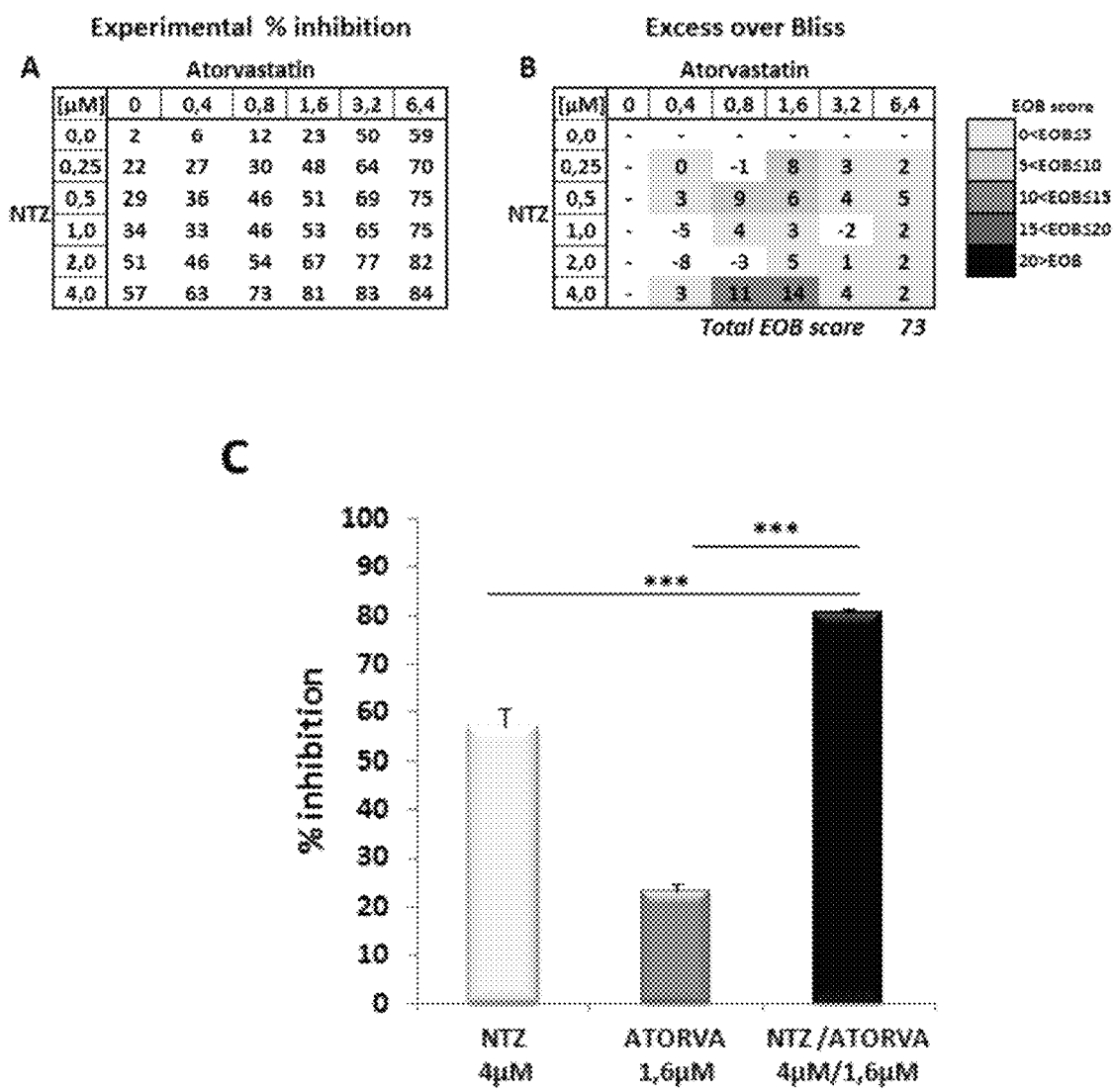

FIG. 7: Combination of NTZ and Atorvastatin Synergistically Inhibit α-SMA in TGFβ-Induced hHSC Combinations were tested in a dose-response matrix format and analyzed according to the excess over Bliss additivism model. Dilution series of NTZ (column) and Atorvastatin (row) were prepared, including their respective DMSO controls. The resulting mixes were added to serum-deprived HSC, 1 hour prior to the activation with the profibrogenic cytokine TGFβ1 (1 ng/ml). (A) Percentage inhibition of α-SMA over the TGFβ1 control. (B) Excess over Bliss (EOB) scores were calculated as described in Materials and Methods. Any compound pair with positive EOB values is considered synergistic (colored from light grey to black), (C) Data values derived from a synergistic combination pair were plotted in a bar graph representation. Data are presented as mean (quadruplicates)±standard deviation (SD). Statistical analyses between single agent vs product combination were performed by student t-test or Mann-Whitney Rank Sum Test using Sigma Plot 11.0 software. [*: $p<0.05$; : $p<0.01$; *: $p<0.001$].

Figure 8:
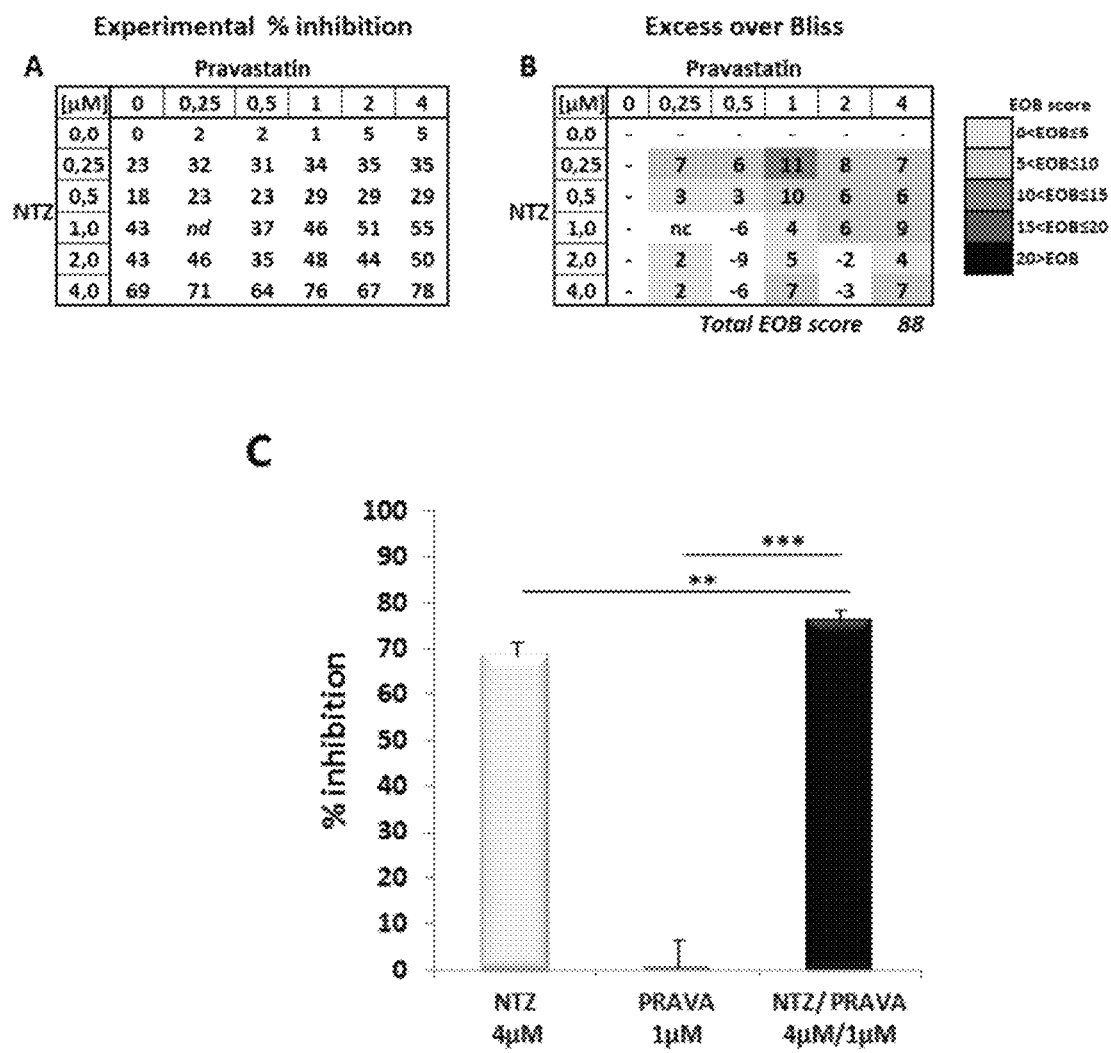

FIG. 8: Combination of NTZ and Pravastatin Synergistically Inhibit α-SMA in TGFβ-Induced hHSC Combinations were tested in a dose-response matrix format and analyzed according to the excess over Bliss additivism model. Dilution series of NTZ (column) and Pravastatin (row) were prepared, including their respective DMSO controls. The resulting mixes were added to serum-deprived HSC, 1 hour prior to the activation with the profibrogenic cytokine TGFβ1 (1 ng/ml). (A) Percentage inhibition of α-SMA over the TGFβ1 control. (B) Excess over Bliss (EOB) scores were calculated as described in Materials and Methods. Any compound pair with positive EOB values is considered synergistic (colored from light grey to black), (C) Data values derived from a synergistic combination pair were plotted in a bar graph representation. Data are presented as mean (quadruplicates)±standard deviation (SD). Statistical analyses between single agent vs product combination were performed by student t-test or Mann-Whitney Rank Sum Test using Sigma Plot 11.0 software. [*: $p<0.05$; : $p<0.01$; *: $p<0.001$].

Figure 9:
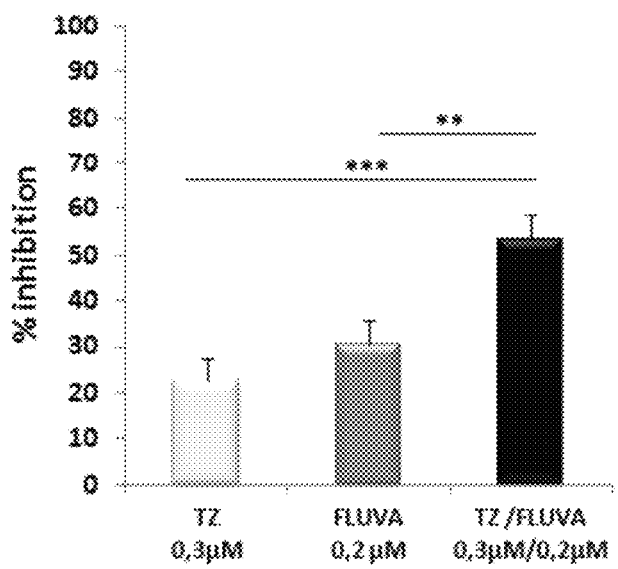

FIG. 9: Fluvastatin Also Synergizes with Tizoxanide, a Metabolite of NTZ, to Reduce Fibrosis in TGFβ-Induced hHSC.

Serum-deprived HSC were preincubated for 1 hour with suboptimal doses of Tizoxanide (TZ). Fluvastatin, or a combination of both products. Data are presented as mean of quadruplicates. Statistical analyses were performed by one-way ANOVA followed by Bonferroni post-hoc tests, using Sigma Plot 11.0 software. [*: $p<0.05$; : $p<0.01$; *: $p<0.001$ (comparison versus 'product combination' group)].

Figure 10:
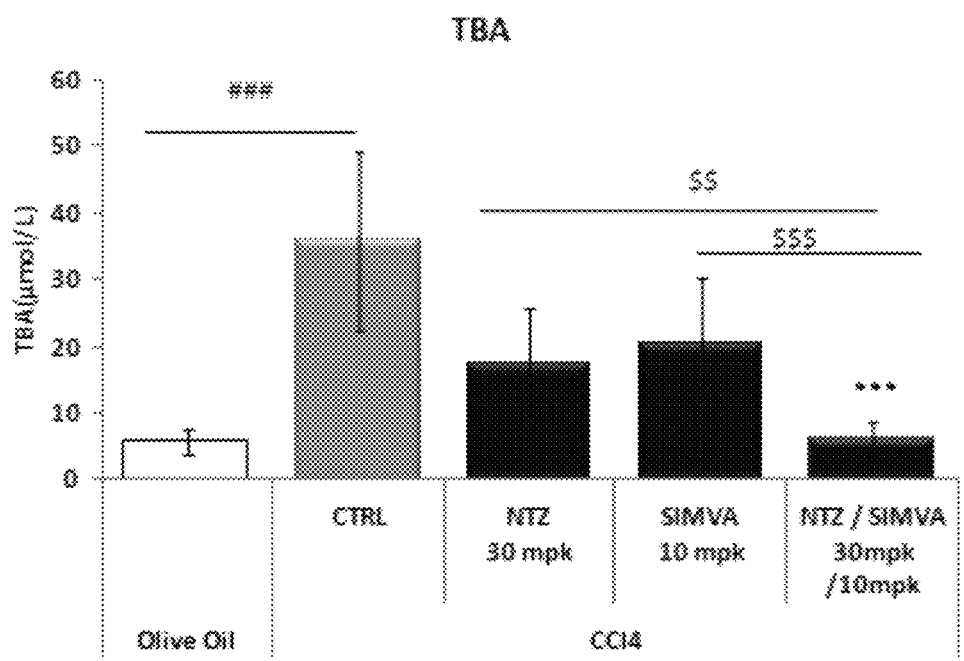

FIG. 10 Combination of NTZ with Simvastatin Synergistically Prevents CCl4-Induced Levels of Circulating TBA Concentration.

250-275 g rats were intraperitoneally injected with olive oil (ctrl group) or with CCl4 emulsified in olive oil (CCl4: olive oil 1:2 v/v, final CCl4 concentration: 2 ml/kg) twice weekly for 3 weeks. Concomitantly, the olive oil injected group was placed on control diet while the CCl4 injected groups were placed on control diet or diet supplemented with NTZ 30 mg/kg/day, SIMVA 10 mg/kg/day or a combination NTZ 30 mg/kg/day/SIMVA 10 mg/kg/day. After the sacrifice, circulating TBA concentration was determined. Data are presented as mean±standard deviation (SD) Statistical analyses were performed using Sigma Plot 11.0 software: Olive Oil vs CCl4: Mann-Whitney Rank Sum Test: ###: $p<0.001$; CCl4 vs CCl4+ cpd treatment: Kruskal Wallis test, followed by Dunn's post ***: $p<0.001$; NTZ/SIMVA combination vs NTZ 30 mpk or SIMVA1 10 mpk: Mann-Whitney Rank Sum Test: $$$$p<0.001$.

Figure 11:
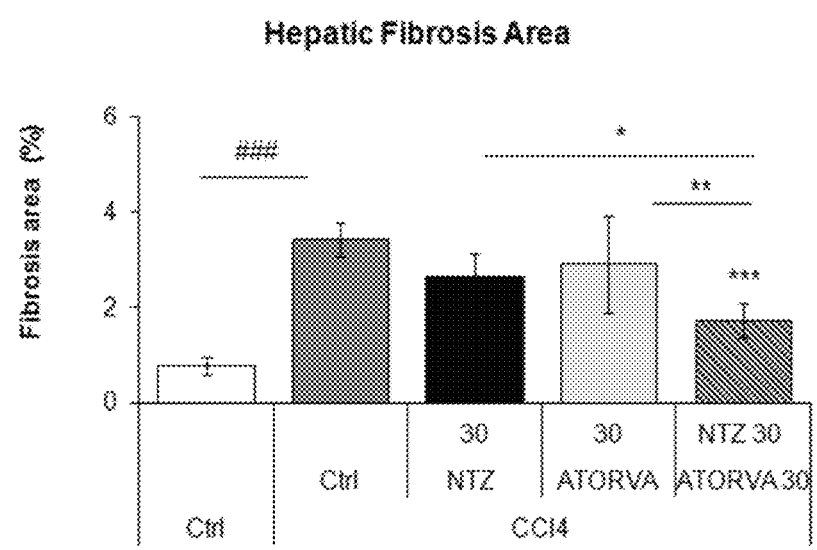

FIG. 11: Combination of NTZ with ATORVA Synergistically Prevents the CCl$_4$-Induced Development of Liver Fibrosis OFA Sprague-Dawley weighing 366 g+/−14 g were intraperitoneally injected with olive oil (control group) or with CCl$_4$ emulsified in olive oil (final CCl$_4$ concentration: 0.75 ml/kg) twice a week for 7 weeks. Concomitantly, the olive oil injected group was placed on control diet whereas the CCl$_4$-injected groups were placed on control diet or diet supplemented with NTZ 30 mg/kg/day, ATV 30 mg/kg/day or the combination of both. After the sacrifice, the percentage of liver fibrosis was determined. Data are presented as mean±standard deviation (SD). Statistical analyses were performed using Prism v7.02 software: Olive Oil and CCl$_4$ groups were compared using Student-t test (#: $p<0.05$; ##: $p<0.01$; ###: $p<0.001$;). The effects of compound treatment vs CCl4 and the synergism of NTZ/ATORVA combination vs NTZ and ATORVA alone (EOHSA model) were evaluated by One-way ANOVA and uncorrected Fisher's LSD post-hoc (*: $p<0.05$; : $p<0.01$; *: $p<0.001$).

DETAILED DESCRIPTION OF THE INVENTION

In the experimental part of the present application, it is shown that a combination of (i) NTZ, or TZ, with (ii) a statin may synergistically confer antifibrotic properties in activated myofibroblasts. Moreover, it is shown that combinations of (i) NTZ or TZ, with (ii) a statin can also reduce altered levels of total biliary acids in a model of liver injury. Accordingly, the present invention relates to a novel synergistic combination of active agents, comprising (i) NTZ or a derivative of NTZ such as a deuterated derivative of NTZ (NTZ-D), TZ or TZG, or a pharmaceutically acceptable salt of NTZ, NTZ-D, TZ or of TZG, and (ii) a statin.

In particular, the present invention relates to the synergistic combination of (i) NTZ, a deuterated derivative of NTZ, or TZ, or a pharmaceutically acceptable salt of NTZ, of TZ, or of a deuterated derivative of NTZ, and (ii) a statin, for use in a method for the treatment of a cholestatic or fibrotic disorder.

Furthermore, the invention relates to the use of the synergistic combination of the invention, comprising (i) NTZ, NTZ-D, TZ or of TZG, or a pharmaceutically acceptable salt of NTZ, NTZ-D, TZ or of TZG, and (ii) a statin, for the manufacture of a medicament useful for the treatment of a cholestatic and fibrotic disorder. The invention also relates to a pharmaceutical composition comprising (i) NTZ, NTZ-D, TZ or of TZG, or a pharmaceutically acceptable salt of NTZ, NTZ-D, TZ or TZG, and (ii) a statin, said components (i) and (ii) acting synergistically as described herein. The pharmaceutical composition according to the invention is useful for treating a cholestatic or fibrotic disorder.

Although the causative agents or initiating events of fibrotic disorders are quite diverse and their pathogenesis is variable, a common feature in affected tissues is the presence of large numbers of activated fibroblasts called myofibroblasts ((Rosenbloom, Mendoza et at, 2013)). Fibrotic stimulus such as TGRβ1 can induce differentiation of fibroblasts to myofibroblasts (Leask and Abraham, 2004; Leask, 2007). Myofibroblasts are metabolically and morphologically distinctive fibroblasts whose activation play a key role during the fibrotic response. Furthermore, these myofibroblasts display unique biological functions including expression of proteins involved in extracellular matrix formation such as different forms of collagen. The induction of α-smooth muscle actin (α-SMA) expression is a recognized hallmark of quiescent fibroblast to activated myofibroblast differentiation and can be used as a physiological read-out to evaluate the potency of the drugs that interfere with the fibrotic process. Tumor Growth β factors, and especially the Tumor Growth Factor beta 1 (TGFβ1) are recognized physiological signals that induce the phenotypic transformation of fibroblasts into profibrotic myofibroblasts that express high levels of α-SMA and high levels of extracellular matrix proteins, which are then secreted and form the fibrotic scar tissue.

Moreover, it is known that the proliferation and the activation of fibroblasts is responsible for the production of several connective tissue components (for example, collagens, elastin, proteoglycans, and hyaluronan) that constitute the extracellular matrix (Kendall and Feghali-Bostwick, 2014).

Unexpectedly, NTZ but also its active metabolite TZ and NTZ deuterated derivatives reveal antifibrotic properties since these compounds dose-dependently reduced the level of α-SMA in TGFβ-induced hepatic stellate cells and in primary fibroblasts from other organs Moreover, NTZ and its metabolite TZ revealed anticholestatic properties by their ability to reduce circulating total bile acids in a model of liver injury.

NTZ, TZ and TZG to be used according to the invention have the following Formula (I), (II) and (III) respectively:

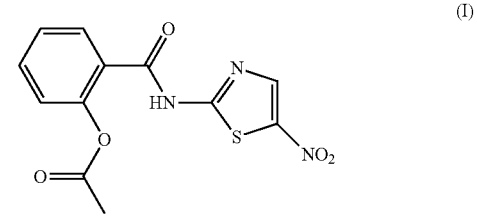

(I)

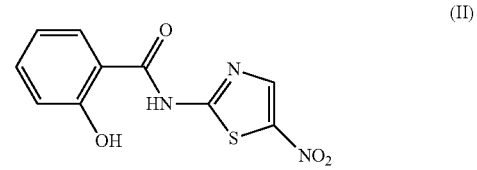

(II)

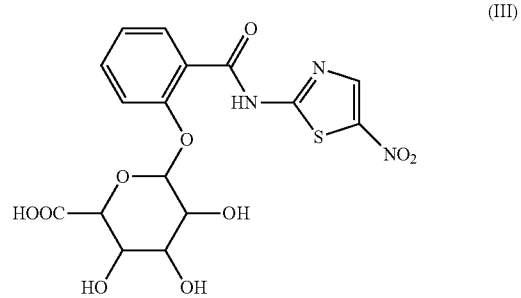

(III)

NTZ and TZ(G) ("TZ(G)" referring to "TZ or TZG")) were known for their antiparasitic and antiviral activities, but the prior art does not teach NTZ, and TZ(G) have anticholestatic and anti-fibrotic effect.

The inventors have demonstrated in a new and inventive way that these compounds have a therapeutic effect in the treatment of cholestasis or fibrosis.

The prior art does neither teach that deuterated derivatives of NTZ (also referred to elsewhere in this application as "NTZ-D") have anticholestatic or anti-fibrotic effects.

According to the present invention, deuterated derivatives of NTZ to be used in the composition according to the invention have the following Formula (IV):

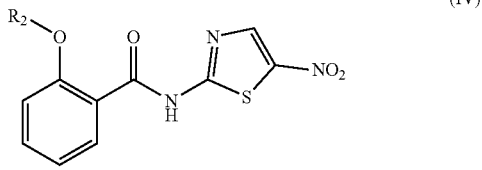

wherein R2 represents a

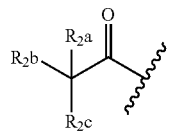

group wherein, R2a, R2b and R2c, identical or different, represent a hydrogen atom or a deuterium atom, with the proviso that R2a, R2b, R2c are not simultaneously a hydrogen atom.

In a particular embodiment. R2a, R2b and R2c represent a deuterium atom.

In a particular embodiment, R2a and R2b represent a deuterium atom, R2c represents a hydrogen atom.

In a particular embodiment, R2a represents a deuterium atom, R2b and R2c represent a deuterium atom.

Examples of such compounds of the invention include:
Cpd.1: 2-[(5-nitro-1,3-thiazol-2-yl)carbarnoyl]phenyl (d3)ethanoate;
Cpd.2: 2-[(5-nitro-1,3-thiazol-2-yl)carbarnoyl]phenyl (d2) ethanoate; and
Cpd.3: 2-[(5-nitro-1,3-thiazol-2-yl)carbamoyl]phenyl (d1) ethanoate;

In the context of the present invention, "NTZ, NTZ-D and TZ(G), and pharmaceutically acceptable salts of NTZ. NTZ-D and TZ(G)" or "compound of formula (I), (II), (III) and (IV), and pharmaceutically acceptable salts of compound of formula (I), (II), (III) and (IV)" are collectively referred to as "component (i)" or "component (i) of the combination".

In the context of the present invention, "component (ii)" or "component (ii) of the combination" refers to "at least one statin" or "a statin".

The inventors have also demonstrated in a new and inventive way that the combination of NTZ, NTZ-D, TZ(G) with a statin may have a synergistic antichoiestatic and/or anti-fibrotic effect in human HSCs.

In the present invention, synergism is defined by a coordinated or correlated action of two or more structures so that the combined action is greater than the sum of each acting separately.

Accordingly, the invention relates to the synergistic combination of (i) NTZ, NTZ-D, TZG, or a pharmaceutically acceptable salt of NTZ, NTZ-D or TZ(G), with (ii) a statin. The invention further relates to this combination, for use in a method for the treatment of a cholestatic or fibrotic disorder.

According to a particular embodiment of the invention, the combination comprises (i) NTZ, NTZ-D or TZ, or a pharmaceutically acceptable salt of NTZE, NTZ-D or TZ, and (ii) a statin.

In a further aspect, the invention relates to the synergistic combination of the invention, for use in the inhibition of proliferation and/or activation of fibroblasts. As is known in the art, fibroblasts are responsible for the production of collagen fibers or other connective tissue components of the extracellular matrix.

According to the present invention, the terms "fibrosis", "fibrotic disease", "fibrotic disorder" and declinations thereof denote a pathological condition of excessive deposition of fibrous connective tissue in an organ or tissue. More specifically, fibrosis is a pathological process, which includes a persistent fibrotic scar formation and overproduction of extracellular matrix, by the connective tissue, as a response to tissue damage. Physiologically, the deposit of connective tissue can obliterate the architecture and function of the underlying organ or tissue.

According to the present invention, the fibrosis or fibrotic disorder may be associated with any organ or tissue fibrosis. Illustrative, non-limiting examples of particular organ fibrosis include liver, gut, kidney, skin, epidermis, endodermis, muscle, tendon, cartilage, heart, pancreas, lung, uterus, nervous system, testis, penis, ovary, adrenal gland, artery, vein, colon, intestine (e.g. small intestine), biliary tract, soft tissue (e.g. mediastinum or retroperitoneum), bone marrow, joint, eye or stomach fibrosis, in particular liver, kidney, skin, epidermis, endodermis, muscle, tendon, cartilage, heart, pancreas, lung, uterus, nervous system, testis, ovary, adrenal gland, artery, vein, colon, intestine (e.g. small intestine), biliary tract, soft tissue (e.g. mediastinum or retroperitoneum), bone marrow, joint or stomach fibrosis.

According to the present invention, the terms "cholestasis" or "cholestatic disease", or "cholestatic disorder" and declinations thereof denote a pathological condition defined by a decrease in bile flow due to impaired secretion by hepatocytes or to obstruction of bile flow through intra- or extrahepatic bile ducts. Therefore, the clinical definition of cholestasis is any condition in which substances normally excreted into bile are retained.

In a particular embodiment, the fibrotic disorder is selected in the group consisting of a liver, gut, lung, heart, kidney, muscle, skin, soft tissue (e.g. mediastinum or retroperitoneum), bone marrow, intestinal, and joint (e.g. knee, shoulder or other joints) fibrosis.

In a preferred embodiment, the fibrotic disorder is selected in the group consisting of the liver, lung, skin, kidney and intestinal fibrosis.

In a more preferred embodiment of the present invention, treated fibrotic disorder is selected in the group consisting of the following non exhaustive list of fibrotic disorders: non-alcoholic steatohepatitis (NASH), pulmonary fibrosis, idiopathic pulmonary fibrosis, skin fibrosis, eye fibrosis, endomyocardial fibrosis, mediastinal fibrosis, myelofibrosis, retroperitoneal fibrosis, progressive massive fibrosis (a complication of coal workers' pneumoconiosis), proliferative fibrosis, neoplastic fibrosis, lung fibrosis consecutive to chronic inflammatory airway disease (COPD, asthma, emphysema, smoker's lung, tubercuiosis), alcohol or drug-induced liver fibrosis, liver cirrhosis, infection-induced liver fibrosis, radiation or chemotherapeutic-induced fibrosis, nephrogenic systemic fibrosis, Crohn's disease, ulcerative colitis, keloid, old myocardial infarction scleroderma/systemic sclerosis, arthrofibrosis, some forms of adhesive capsulitis, chronic fibrosing cholangiopathies such as Primary Sclerosing Cholangitis (PSC) and Primary Biliary Cholangitis (PBC), biliary atresia, familial intrahepatic cholestasis type 3 (PFIC3), peri-implantational fibrosis and asbestosis.

According to a particular embodiment of the invention, the cholestestatic disease is selected in the group consisting of primary biliary cholangitis (PBC), primary sclerosing cholangitis (PSC), Intrahepatic Cholestasis of Pregnancy, Progressive Familial Intrahepatic Cholestasis, Biliary atresia, Cholelithiasis, Infectious Cholangitis, Cholangitis associated with Langerhans cell histiocytosis, Alaqilie syndrome, Nonsyndromic ductal paucity, Drug-induced cholestasis, and Total parenteral nutrition-associated cholestasis. In a preferred embodiment, the cholestatic disease is PBC or PSC, in particular PBC.

The term "treatment" or "treating" refers to the curative or preventive of a cholestatic or fibrotic disorder in a subject in need thereof. The treatment involves the administration of the combination of the invention to a subject having a declared disorder, i.e, to a patient, to cure, delay, reverse, or slow down the progression of the disorder, improving thereby the condition of the subject. A treatment may also be administered to a subject that is healthy or at risk of developing a cholestatic or fibrotic disorder to prevent or delay the disorder.

Therefore, according to the invention, the treatment of a fibrotic disorder involves the administration of the combination of the present invention, for example in the form of a pharmaceutical composition containing components (i) and (ii) of the combination, to a subject having a declared disorder to cure, delay, reverse or slow down the progression of the disorder, thus improving the condition of the patient or to a healthy subject, in particular a subject who is at risk of developing a cholestatic or fibrotic disorder.

The subject to be treated is a mammal, preferably a human. The subject to be reated according to the invention can be selected on the basis of several criteria associated with cholestatic or fibrotic diseases such as previous drug treatments, associated pathologies, genotype, exposure to risk factors, viral infection, as well as on the basis of the detection of any relevant biomarker that can be evaluated by means of imaging methods and immunological, biochemical, enzymatic, chemical, or nucleic acid detection methods.

According to the present invention, the term "statin(s)" refers the HMG-CoA reductase inhibitors, which are a class of cholesterol lowering drugs that inhibit the enzyme HMG-CoA reductase, which plays a central role in the production of cholesterol. Elevated blood cholesterol levels have been associated with cardiovascular disease (CVD), and many studies have shown that the risk of CVD events can be reduced by lipid-lowering therapy. At the beginning, the lipid-lowering armamentarium was limited essentially to a low saturated fat and cholesterol diet, bile acid sequestrants (cholestyramine and colestipol), nicotinic acid (niacin), fibrates and probucol. Unfortunately, all of these treatments have limited efficacy or tolerability, or both.

The HMG-CoA reductase inhibitors described above belong to a structural class of compounds which contain a moiety which can exist as either a 3-hydroxy lactone ring or as the corresponding ring opened dihydroxy open-acid. Salts of the dihydroxy open-acid can be prepared, and in fact, as noted above, several of the marketed statins are administered as the dihydroxy open add salt forms.

For example, lovastatin and simvastatin are marketed worldwide in their lactonized form.

Statins have been found to reduce cardiovascular disease and mortality in those who are at high risk. The evidence is strong that statins are effective for treating CVD in the early stages of a disease (secondary prevention) and in those at elevated risk but without CVD (primary prevention).

According to the invention, the term "statin(s)" used herein includes, but s not limited to fluvastatin, atorvastatin, mevastatin, cerivastatin, lovastatin, simvastatin, rosuvastatin, pravastatin, and pitavastatin. According to a particular embodiment of the invention, the statin is selected from pitavastatin, fluvastatin, simvastatin and atorvastatin.

Statins may be in the form of a salt, hydrate, solvate, polymorph, or a co-crystal. Statins may also be in the form of a hydrate, solvate, polymorph, or a co-crystal of a salt. Statins may also be present in the free acid of lactone form according to the present invention.

Component (ii) of the combination may comprise one or more statin, i,e, one statin or a mixture of statins.

According to the invention the statin comprised in the combination of the invention is selected so that the combination of said statin and component (i) of the combination of the invention provides a synergistic action against cholestasis or fibrosis. Such synergy may be determined according to methods well-known in the art, such as by using the Excess Over Bliss (EOB) method described in the examples.

In a preferred embodiment, the statin in the synergistic combination of the present invention is selected in the group consisting of lovastatin, rosuvastatin, pravastatin, pitavastatin, fluvastatin, simvastatin and atorvastatin, in particular in the group consisting of pitavastatin, fluvastatin and simvastatin.

Another aspect of the invention relates to the synergistic combination described above in the form of a pharmaceutical composition. Therefore, the invention also relates to a pharmaceutical composition comprising (i) NTZ, NTZ-D or TZ(G), or a pharmaceutically acceptable salt of NTZ, NTZ-D or TZ(G), and (ii) a statin.

In yet another aspect, the present invention relates to the synergistic combination described above, in the form of a kit-of-parts for the simultaneous sequential or separate administration of its components, as described in more details below.

The invention provides also a method of treatment of cholestasis or fibrosis.

The treatment involves the administration of the synergistic combination of the invention to a patient having a declared disorder to cure, delay, or slow down the progress, thus improving the condition of the patent or to a healthy subject, in particular a subject who is at risk of developing a cholestatic or fibrotic disease, to prevent the disease.

The subjects to be treated according to the invention can be selected on the basis of several criteria associated to fibrotic diseases such as previous drug treatments, associated pathologies, genotype, exposure to risk factors, viral infection, as well as any other relevant biomarker that can be evaluated by means of imaging methods and immunological, biochemical, enzymatic, chemical, or nucleic acid detection method.

Synthesis of NTZ or TZ can be for example carried out as described in (Rossignol and Caviar, 1975), or by any other way of synthesis known by a person skilled in the art. TZG can be, for example, synthesized according to way of synthesis known in the art such as in Wadouachi 2011.

In a particular embodiment, the treatment of a cholestatic or fibrotic disorder may comprise the administration of a composition comprising at least two compounds selected from NTZ, NTZ-D and TZ(G). In this embodiment, the administered statin is provided in the same composition as the two compounds, or in a separate form, such as in a different composition.

In another embodiment, the synergistic combination of the invention is for simultaneous, sequential or separate administration in therapy, therefore being possibly included in different compositions. In case of sequential administration, component (i) of the combination may be administrated prior to component (ii), or component (ii) is administrated prior to component (i). As such, the invention also relates to kit-of-parts comprising the synergistic combination of (i) NTZ, NTZ-D and TZ(G), or a pharmaceutically acceptable salt of NTZ, NTZ-D and TZ(G), and (ii) a statin, for simultaneous, sequential or separate administration.

NTZ, NTZ-D, TZ(G) and a statin can be formulated as pharmaceutically acceptable salts, particularly acid or base salts compatible with pharmaceutical use. Salts of NTZ, NTZ-D, TZ(G) and a statin include pharmaceutically acceptable acid addition salts, pharmaceutically acceptable base addition salts, pharmaceutically acceptable metal salts, ammonium and alkylated ammonium salts. These salts can be obtained during the final purification step of the compound or by incorporating the salt into the previously purified compound.

Combination of a components (i) and (ii), in particular of a compound of Formula (I), (II), (III) or (IV) with one or more statin(s) can be formulated as pharmaceutically acceptable non-toxic salts obtained from organic or inorganic bases or acids of compound of Formula (I), (II), (III) (IV) or statin(s). These salts can be obtained during the final purification step of the compound or by incorporating the salt into the previously purified compound.

The pharmaceutical compositions of the present invention comprising component (i) and/or (ii), in particular comprising a compound of Formula (I), (II), (III) and/or one or more statin(s) can also comprise one or several excipients or vehicles, acceptable within a pharmaceutical context (e.g. saline solutions, physiological solutions, isotonic solutions, etc., compatible with pharmaceutical usage and well-known by one of ordinary skill in the art).

These compositions can also comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc.

These compositions can be formulated in the form of injectable suspensions, gels, oils, ointments, pills, tablets, suppositories, powders, gel caps, capsules, aerosols, etc., eventually by means of galenic forms or devices assuring a prolonged and/or slow release. For this kind of formulation, agents such as cellulose, carbonates or starches can be advantageously used.

The pharmaceutical compositions of the present invention comprising component (i) and/or (ii) of the combination, such as a compound of Formula (I), (II), (III) and/or one or more statin(s) (the statin being selected, as mentioned above, among those that allows a synergistic effect with component (i) of the combination of the present invention) may be administered by different routes and in different forms. For example, the compound(s) may be administered via a systemic way, per os, parenterally, by inhalation, by nasal spray, by nasal instillation, or by injection, such as for example intravenously, by intra-muscular route, by subcutaneous route, by transdermal route, by topical route, by intra-arterial route, etc.

Of course, the route of administration will be adapted to the form of component (i) in combination with one or more statin(s) according to procedures well known by those skilled in the art.

In a particular embodiment, the component(s) (i) and (ii) are formulated as a tablet or as tables. In another particular embodiment, the compounds are administered orally.

NTZ, NTZ-D or TZ(G) in combination with one or more statin(s) is administered in a therapeutically effective amount. Within the context of the invention, the term "effective amount" refers to an amount of the compound sufficient to produce the desired therapeutic result.

The frequency and/or dose relative to the administration can be adapted by one of ordinary skill in the art, in function of the patient, the pathology, the form of administration, etc. Typically, the combination (such as in the form of a pharmaceutical composition or a kit-of-parts) of the present invention can be administered for the treatment of a cholestatic or fibrotic disease at a dose for component (i) of the combination comprised between 0.01 mg/day to 4000 mg/day, such as from 50 mg/day to 2000 mg/day, such as from 100 mg/day to 2000 mg/day; and particularly from 100 mg/day to 1000 mg/day. In a particular embodiment, the NTZ, TZ(G), or a pharmaceutically acceptable salt thereof, is administered at a dose of about 1000 mg/day (i.e at a dose of 900 to 1100 mg/day), in particular at 1000 mg/day. In a particular embodiment, NTZ, TZ(G), or a pharmaceutically acceptable salt thereof, is administered orally at a dose of about 1000 mg/day, in particular at 1000 mg/day, in particular as a tablet. Administration can be performed daily or even several times per day, if necessary. In one embodiment, the compound is administered at least once a day, such as once a day, twice a day, or three times a day. In a particular embodiment, the compound is administered once or twice a day. In particular, oral administration may be performed once a day, during a meal, for example during breakfast, lunch or dinner, by taking a tablet comprising the compound at a dose of about 1000 mg, in particular at a dose of 1000 mg. In another embodiment, a tablet is orally administered twice a day, such as by administering a first tablet comprising the compound at a dose of about 500 mg (i.e. at a dose of 450 to 550 mg), in particular at a dose of 500 mg, during one meal, and administering a second tablet comprising the compound at a dose of about 500 mg, in particular at a dose of 500 mg, during another meal the same day.

The dose of the statin in the said combination may vary according to the statin itself. The dose is adapted to the efficiency of the statin according to typical statin regimen.

For example, for Fluvastatin, the dose may be comprised between 10 to 50 mg/day, and particularly from 20 to 40 mg/day.

For pitavastatin the dose may be comprised between 0.1 mg/day to 6 mg/day, and particularly from 1 to 4 mg/day.

For both Simvastatin and Atorvastatin, the dose may be comprised between 1 mg/day to 100 mg/day, and particularly from 10 to 80 mg/day.

In a preferred embodiment of the invention, component (i), in particular NTZ, is used in combination with fluvastatin at a dose comprised between 100 mg/day to 1000 mg/day for NTZ and 1 to 4 mg/day for fluvastatin.

In another preferred embodiment of the invention, component (i), in particular NTZ, is used in combination with pitavastatin at a dose comprised between 100 mg/day to 1000 mg/day for NTZ and 1 to 4 mg/day for pitavastatin.

In another preferred embodiment of the invention, component (i), in particular NTZ, is used in combination with Simvastatin or Atorvastatin at a dose comprised between 100 mg/day to 1000 mg/day for NTZ and 10 to 80 mg/day for Simvastatin and Atorvastatin.

In another preferred embodiment, the active ingredients are administered as one or more pharmaceutical composition(s) in the form of a pill or tablet intended for an oral ingestion.

Administration can be performed daily or even several times per day, if necessary.

Suitably, the course of treatment with the combination of the invention is for at least 1 week, in particular for at least 2, 3, 4, 5, 6, 7, 8, 9, 10, 15, 20 or 24 weeks or more. In particular, the course of treatment with NTZ, TZ(G) or a pharmaceutically acceptable salt thereof is for at least 1 year, 2 years, 3 years, 4 years or at least 5 years.

In a particular embodiment, the invention relates to the treatment of a cholestatic or fibrotic disease, in particular liver fibrosis, more particularly liver fibrosis consecutive to NASH, in a patient in need thereof, comprising administering to said patient a therapeutically effective amount of the combination of the invention, including in particular administering NTZ at a dose of 1000 mg/day, in particular by administering a tablet containing 500 mg of NTZ twice a day, in particular during two different meals.

In a particular embodiment, the invention relates to a combination of the present invention, further combined to at least one other therapeutically active agent, such as other molecules with known antifibrotic activity. This further combination of the present invention is useful for the treatment of a cholestatic or fibrotic disorder.

According to a variant of this embodiment, NTZ, TZ or a deuterated derivative of NTZ in combination with one or more statin(s) can be combined with any antifibrotic compound such as pirfenidone or receptor tyrosine kinase inhibitors (RTKIs) such as Nintedanib, sorafenib and other RTKis, or angiotensin II (AT1) receptor blockers, or CTGF inhibitor, or any antifibrotic compound susceptible to interfere with the TGFβ- and BMP-activated pathways including activators of the latent TGFβ complex such as MMP2, MMP9, THS BS1 or cell-surface integrins, TGFβ receptors type I (TGFBRI) or type II (TGFBRII) and their ligands such as TGFβ, Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinaese/AKT pathways, TGFβ-induced EMT process of canonical and non-canonical Hedgehog signaling pathways including Hh ligands or target genes, or any members of the WNT, or Notch pathways which are susceptible to influence TGFβ signaling.

Thus, the invention also relates to a pharmaceutical composition, in particular for its use in a method for the treatment of a cholestatic or fibrotic disease, comprising a compound selected from component (i) with component (ii), in combination with at least one therapeutically active agent with known antifibrotic activity selected from pirfenidone or receptor tyrosine kinase inhibitors (RTKIs) such as Nintedanib, sorafenib and other RTKIs, or angiotensin II (AT1) receptor blockers, or CTGF inhibitor, or antifibrotic compound susceptible to interfere with the TGFβ- and BMP-activated pathways including activators of the latent TGFβ complex such as MMP2, MMP9, THBS1 or cell-surface integrins, TGFβ receptors type I (TGFBRI) or type II (TGFBRII) and their Uganda such as TGFβ, Activin, inhibin, Nodal, anti-Müllerian hormone, GDFs or BMPs, auxiliary co-receptors (also known as type III receptors), or components of the SMAD-dependent canonical pathway including regulatory or inhibitory SMAD proteins, or members of the SMAD-independent or non-canonical pathways including various branches of MAPK signaling, TAK1, Rho-like GTPase signaling pathways, phosphatidylinositol-3 kinase/AKT pathways, TGFβ-induced EMT process, or canoninal and non-canonical Hedgehog signaling pathways including Hh ligands or target genes, or any members of the WNT, or Notch pathways which are susceptible to influence TGFβ signaling, for use in a method for treating a cholestatic or fibrotic disorder.

In another particular embodiment, other classes of molecules that could also be combined with component (i) and component (ii) include JAK/STAT inhibitors, or other anti-inflammatory and/or immunosuppressant agents. The non exhaustive list of these agents includes but is not limited to glucocorticoids, NSAIDS, cyclophosphamide, nitrosoureas, folic acid analogs, purine analogs, pyrimidine analogs, methotrexate, azathioprine, mercaptopurine, ciclosporin, mynocin, tacrolimus, sirolimus, mycophenolic acid derivatives, fingolimod and other sphingosine-1-phosphate receptor modulators, monoclonal and/or polyclonal antibodies against such targets as proinflammatory cytokines and proinflammatory cytokine receptors, T-cell receptor, integrins. Other classes of molecules that could also be combined with component (i) and component (ii), include molecules that could potentially enhance the exposure or the effect of component (i) with component (ii).

In another embodiment, components (i) and (ii), are administered as the sole active ingredient.

In a further embodiment, the present invention provides methods of treating a cholestatic or fibrotic disease comprising the administration of the combination of the present invention, in particular in the form of a pharmaceutical composition or of a kit-of-parts containing component (i) and component (ii).

The invention is further described with reference to the following, non-limiting, examples.

EXAMPLES

Materials and Methods

Compounds were dissolved in dimethyl sulfoxide (DMSO, Fluka cat #41640). Nitazoxanide (INTERCHIM cat # RQ0550U), tizoxanide (INTERCHIM cat # RP253) were obtained commercially, as well as Pitavastatin (INTERCHIM cat #15414), Simvastatin (Sigma Aldrich cat # S6196), Fluvastatin (Sigma Aldrich cat # Y0001090), Pravastatin (Selleckchem cat # S3036), Rosuvastatin (Selleckchem cat # S2169), Lovastatin (Selleckchem cat # S4223), Atorvastatin (Sigma Aldrich cat # PZ0001).

hHSC Culture

The human primary hepatic stellate cells (hHSC) (Innoprot) were cultured in STeCM medium (ScienCell cat #5301) that was supplemented with 2% fetal bovine serum (FBS, ScienCell cat #0010), 1% penicillin/streptomycin (ScienCell cat #0503) and stellate cell growth supplement (SteCGS; ScienCell cat #5352). Cell-culture flasks were coated with Poly-L Lysine (Sigma cat # P4707) for a better adherence.

Preparation of Compositions

2 Components Combination Matrix (NTZ/Statin or TZ/Statin)

The checkerboard matrix was adopted. NTZ or TZ and statin stocks were serially diluted in DMSO in a 5-points series in a row (statin) and a column (NTZ or TZ) of a 96-well plate. A $6^{th}$ point was filled with 100% DMSO without compound. Subsequently, the 6×6 combination matrix was generated by 1:1 mixing of all single agent concentrations. The five test concentrations for each compound were chosen based on the respective $IC_{50}$ of each compound as single agent obtained by measuring α-SMA content in the HSC model stimulated with TGF-β1. Then, 2-fold and 4-fold higher and lower concentrations were selected.

For Pravastatin and Rosuvastatin which were found inactive and weak inhibitor, respectively in TGF-β1 stimulated HSC model, the dose range was selected arbitrarily (5 doses serially diluted 2 fold starting from 4 µM).

Activation of hHSC with TGF-β1 and Compound Treatment

The human primary hepatic stellate cells (hHSC) (Innoprot) were cultured under standard conditions, as described above. The cells were subsequently plated at a density of $2 \times 10^4$ cells/well into 96-well plates for the measure of α-SMA by ELISA. The next day, cell culture medium was removed, and cells were washed with PBS (Invitragen cat #14190). hHSC were deprived for 24 hours in serum-free and SteCGS-free medium. For the treatments with NTZ, statins (Pitavastatin, Fluvastatin, Simvastatin, Atorvastatin, Lovastatin, Rosuvastatin, Pravastatin) and the respective NTZ/statin combinations and also for the treatment with TZ, statins (Pitavastatin, Simvastatin, Fluvastatin, Pravasatin) and the respective combinations TZ/statin, the serum-deprived hHSC were preincubated for 1 hour with the compounds followed by the addition of the profibrogenic stimuli TGF-β1 (PeproTech cat #100-21, 1 ng/mL) in serum-free and SteCGS-free medium for an additional 48 hour period.

At the end of treatment, cells were washed with PBS (Invitrogen, cat #14190) before the addition of 50 µl of lysis buffer (CelLytic™ MT reagent; Sigma # C3228). Plates were then incubated for 30 min on ice using a plate shaker, before storage at −20° C.

α-SMA ELISA

The level of α-SMA was, measured using a Sandwich ELISA. Briefly, the wells of an ELISA plate were first coated with the capture antibody (mouse monoclonal anti-ACTA2, Abnova) at 4° C., overnight. After 3 washes in PBS+0.2% Tween 20, a blocking solution consisting of PBS+0.2% BSA was added for one hour followed by another washing cycle. The cell lysates were transferred into the wells for binding to the capture antibody for a period of 2 h at room temperature. After the washing procedure, the detection antibody (biotinylated mouse monoclonal anti-ACTA2, Abnova) was added for 2 hours at room temperature followed by 3 washes. For the detection, an HRP-conjugated Streptavidin (R&D Systems cat # DY998) was first applied for 30 min at room temperature. After washing, the HRP substrate TMB (BD, #555214) was added and incubated for 7 min at room temperature in the dark. Upon oxidation, TMB forms a water-soluble blue reaction product that becomes yellow with addition of sulfuric acid (solution stop), enabling accurate measurement of the intensity at 450 nm using a spectrophotometer. The developed color is directly proportional to the amount of α-SMA present in the lysate.

Determination of Synergism by Excess Over Bliss (EOB) Method

The values obtained in the αSMA ELISA assays were first transformed into percentage inhibitions over TGF-β1 control. Then, using these percentage inhibitions converted into fractions (percentage divided by 100), EOB (Excess Over Bliss) was determined to define the synergistic effects of drug combinations. Expected Bliss additivism score (E) was firstly determined by the equation:

$E = (A+B) - (A \times B)$ where A and B are the percentage inhibitions converted into fractions within a range of 0 to 1 of NTZ (A) and a given statin (B) at a given dose. The difference between the Bliss expectation and the observed inhibition of the combined NTZ/statin at the same dose is the 'Excess over Bliss' score.

Excess over Bliss score=0 indicates that the combination treatment is additive as expected for independent pathway effects);

Excess over Bliss score>0 indicates activity greater than additive (synergy); and Excess over Bliss score<0 indicates the combination is less than additive (antagonism).

For each product combination (NTZ+statin), an additional total Bliss score was calculated by summation of all EOB.

Confirmation of Synergism by EOHSA (Excess Over Highest Single Agent Method)

EOHSA is a standard measure of synergy used by the FDA for evaluation of drug combinations and is calculated as the difference of the effect produced by the drug combination and the greatest effect produced by each of the combination's single agents at the same concentrations as when combined (Borisy et al., 2003).

In vitro, to validate the synergism, the experimental values corresponding to top EOB score for each NTZ/statin combination were plotted in a bar graph. The significance of the observed differences between NTZ/statin or TZ/statin and single agents were estimated by a student t-test or Mann-Whitney Rank Sum Test using Sigma Plot 11.0 software. [*: $p<0.05$; : $p<0.01$; *: $p<0.001$].

In vivo, the significance of the observed differences between NTZ/statin or and single agents were estimated using One-way ANOVA and uncorrected Fishers LSD post-hoc [*: $p<0.05$; : $p<0.01$; *: $p<0.001$].

Evaluation of the Synergistic Therapeutic Effect of NTZ/SIMVA Combination in CCl4-Induced Liver Fibrosis The synergistic therapeutic effect of NTZ/SIMVA combination was assessed in a rat model of CCl4-induced liver injury.

OFA S; Dawley rats (initial body weight 250-275 g) were randomized according to their body weight into 5 groups and treated for 3 weeks. The rats were intraperitoneally injected with olive oil (ctrl group) or with CCl4 emulsified in olive oil (CCl4: olive oil 1:2 v/v, final CCl4 concentration: 2 ml/kg) twice weekly. Concomitantly, the olive oil injected group was placed on control diet while the CCl4 injected groups were placed on control diet or diet supplemented with compounds. 3 regimens were prepared corresponding respectively to an exposure of NTZ 30 mg/kg/day, SIMVA 10 mg/kg/day or NTZ/SIMVA 30/10 mg/kg/day. The last day of treatment, the rats were sacrificed after a 6 h fasting period. Blood samples were collected and the serum was isolated for biochemical analyses.

Evaluation of NTZ/ATORVA Combinations in a Chronic $CCl_4$-Induced Liver Fibrosis Model (7 wks)

9-week-old male Sprague-Dawley rats (initial body weight ~365 g) were placed on control diet or diet supplemented with NTZ alone, ATORVA alone, or combination of NTZ/ATORVA for 7 weeks. 3 regimens containing the compounds were prepared corresponding to an exposure of NTZ 30, ATORVA 30 and NTZ/ATORVA 30/30 mg/kg/day. Concomitantly, rats were treated twice a week for 7 weeks with CCl4 (0.75 ml/kg) dissolved in olive oil or vehicle by intraperitoneal injections. The body weight and the food intake were monitored twice a week. The last day of treatment, the rats were sacrificed after a 6 h fasting period. Blood samples were collected and the serum was isolated for biochemical analyses. The liver was rapidly excised for biochemical and histological studies.

Evaluation of the Synergistic Therapeutic Effect of NTZ/SIMVA Combination in a DDC-Induced Cholestasis Model:

The synergistic therapeutic effect of NTZ/SIMVA combination will be assessed in a DDC-induced cholestasis model.

C57BL/6 mice will be fed for 8 weeks a 0.1% DDC-supplemented diet, or 0.1% DDC-supplemented diet corresponding respectively to an exposure of NTZ 100 mg/kg/day, or SIMVA 10 mg/kg/day or a standard mouse diet (Ssniff). The last day of treatment, the mice will be sacrificed after a 6 h fasting period Blood samples will be taken for biochemical analyses and liver will be rapidly excised for biochemical and histological studies.

Evaluation of the Synergistic Therapeutic Effect of NTZ/SIMVA Combination in a Chronic CCl4-Induced Liver Fibrosis Model 9 week-old C57BL/6 mice will be placed on control diet or diet supplemented with NTZ for 6 weeks. 8 diet regimen containing NTZ and/or SIMVA will be prepared corresponding respectively to an exposure of NTZ at 30 or 100 mg/kg/day or SIMVA at 3 or 10 mg/kg/day or a combination of NTZ/SIMVA 30/3; 100/3; 30/10,100/10 mg/kg/day, respectively. Concomitantly, and for the total duration of 6 weeks, the mice will be treated 3 times a week with CCl4 dissolved in olive oil or vehicle by oral gavage. The amount of CCl4 will be progressively increased from 0.875 ml/kg to 2.5 ml/kg. The last day of treatment, the mice will be sacrificed after a 6 h fasting period. Blood samples will be collected and the serum will be isolated for biochemical analyses. The liver will be rapidly excised for biochemical, histological & expression studies.

Evaluation of the Synergistic Therapeutic Effect of NTZ/SIMVA Combination in a BDL Model Surgical bile duct ligation will be performed on rats in order to induce an extrahepatic cholestasis and subsequently liver fibrosis. After a short recovery period, animals will be treated with NTZ at 30 or 100 mg/kg/day, SIMVA at 3 or 10 mpk, or combinations of NTZ/SIMVA 30/3, or 100/10 mg/kg/day for one or two weeks. The last day of treatment, the mice will be sacrificed after a 6 h fasting, period. Blood, samples will be collected and the serum will be isolated for biochemical analyses. The liver will be rapidly excised for biochemical, histological & expression studies.

Measurement of Plasmatic Concentration of Total Bile Acids

The plasmatic concentration of Total Bile Acids (IBA) was determined using the appropriate Randox kit for the Daytona automated Analyzer (Randox, cat # BI3863). In the presence of Thio-NAD, the enzyme 3-α hydroxysteroid dehydrogenase (3-α HSD) converts bile acids to 3-keto steroids and Thio-NADH. The reaction is reversible and 3-α HSD can convert 3-ketosteroids and Thio-NADFH-to bile acids and Thio-NAD. In the presence of excess NADH, the enzyme cycling occurs efficiently and the rate of formation of Thio-NADH is determined by measuring specific change of absorbance at 405 nm. Results are expressed in μmol/L.

Histology

At sacrifice, liver pies were prepared for histological analysis d examined as described below.

Tissue Embedding and Sectioning:

The liver slices were first fixed for 16 hours in formalin 4% solution followed by several; dehydration steps in ethanol (successive baths at 70, 80, 95 and 100% ethanol). The liver pieces were subsequently incubated in a xylene bath followed by 3 baths in liquid paraffin (60° C.). Liver pieces were then put into, small racks that were gently filled with Histowax® to completely cover the tissue.

Picrosirius Red Staining

The 3 μm paraffin sections of the liver were stained for collagen fibers as follows. Liver sections were deparaffinized, rehydrated and incubated for 15 minutes in a solution of Fast Green FCF 0.04% (Sigma-Aldrich, cat # F7258) before rinsing in a bath of 0.5% acetic acid (Panreec, cat #131008.1611). Then, the liver sections were rinsed in water and incubated 30 minutes in a solution of Fast Green FCF 0.04%-0.1% sinus red (Direct Red 80, Fluke cat #43665) in saturated aqueous picric acid (Sigma-Aldrich cat # P6744). Sections were then dehydrated, and mounted using the CV Mount medium (Leica, cat #14046430011).

Measurement of Hepatic Collagen Content

The hepatic collagen content was determined using the appropriate QuickZyme kit (Total collagen assay, cat # QZB-totcol2). The assay is based on the detection of hydroxyproline, which is a non-proteinogenic amino acid mainly found in the triple helix of collagen. Thus, hydroxyproline in tissue hydrolysates can be, used as an indirect measure of the amount of collagen present in the tissue (without discrimination between procollagen, mature collagen and collagen degradation products).

Complete hydrolysis of tissue samples in 6M HCl at 95° C. is required before dosing the hydroxyproline. The assay results in the generation of a chromogen with a maximum absorbance at 570 nm. Results are expressed as mg of collagen/g of liver.

Results and Conclusions:

The abnormal persistence of differentiated myofibroblasts is a characteristic of many fibrotic diseases. Following liver injury, quiescent HSCs undergo a process of activation that is characterized by a differentiation into (α-SMA)-positive myofibroblasts. In an attempt to find new antifibrotic molecules, a library of FDA-approved drugs was phenotypically screened in a model of human HSC activated with the profibrogenic cytokine TGF-β1. The level of β-SMA, a hallmark of fibrotic lesions, was used to evaluate the potency of the drugs to interfere with the fibrotic process. The screening campaign led to the identification of nitazoxanide (NTZ), which dose-dependently reduced the level of α-SMA in TGFβ-induced HSGs. Overall, NTZ exhibited an $IC_{50}$ comprised between 0.1 and 3 μM (FIG. 1A).

Since it is known that NTZ is rapidly hydrolyzed into its active metabolite tizoxanide (TZ) (Broekhuysen, Stockis et al., 2000), this metabolite was also evaluated for its antifibrotic activity in HSC. TZ showed a profile similar to the parent drug with an $IC_{50}$ comprised between 0.1 and 3 μM (FIG. 1B). Interestingly, specific statins but not all were also identified during the screening campaign. The dose-response analyses performed in the TGFβ-induced HSC model (FIG. 2) reveal that the 7 tested statins are not equivalent regarding their antifibrotic properties.

Typically, Pitavastatin (FIG. 2A) and Fluvastatin (FIG. 2B), the most potent antifibrotic statins, exhibited an $IC_{50}$ below 1 μM whereas the values of Simvastatin (FIG. 2C), Atorvastatin (FIG. 2D), Lovastatin (FIG. 2E) were generally comprised between 1 and 3 μM. Rosuvastatin (FIG. 2F) revealed a significant antifibrotic activity but only at the highest doses and Pravastatin (FIG. 2G) was found inactive alone at the tested doses. It is noteworthy that the antifibrotic properties of the various statin family members do not seem to be related to their lipid lowering capacity. For example, Rosuvastatin, which is considered the most potent statin for HMG_CoA reductase Inhibition (IC50=5.4 nM; (McKenney, 2003) revealed weak antifibrotic properties. In order to evaluate if a combination of statin with NTZ or TZ could reduce fibrosis in a synergistic manner, combination matrix experiments were performed in TGFβ-induced HSCs. Briefly, NTZ or TZ and statin solutions were serially diluted in a checkerboard format generating a 36 combinations matrix covering a large panel of statin/NTZ or statin/TZ ratios. Synergy was first determined by calculating Excess Over Bliss scores, in order to rank the different statins based on their synergism, the sum of the EOB scores obtained for each statin was also calculated. These experiments revealed that NTZ could synergize with all statins, but not with the same potency, to reduce α-SMA production in activated HSCs.

The best synergy was obtained with NTZ in combination with Pitavastatin (total EOB score of 337), followed by Sirnvastatin (total EOB score of 255), Fluvastatin (total EOB score of 141), Lovastatin (total EOB score of 91), Pravastatin (total EOB score of 88), and Atorvastatin (total EOB score of 73) (FIGS. 4B, 5B, 6B, 7B and 8B). Positive EOB score were obtained only for a few NTZ/ROSU ratios (data not shown) indicating a synergy, but weaker, comparatively to the other NTZ/statin combinations. To validate the synergism, the experimental values corresponding to high the EOB score for each NTZ/statin combination were plotted in a bar graph (FIGS. 4C, 5C, 6C, 7C, and 8C).

These graphs illustrate that the combination of NTZ with Pitavastatin, Simvastatin, Fluvastatin, Lovastatin, Atorvastatin and Pravastatin show a superior antifibrotic effect that is statistically significant compared to the highest single agent (NTZ or statin). The most impressive examples are represented with Pitavastatin, Simvastatin, or Fluvastatin in which the single agents provide a weak antifibrotic activity (~10 to 20% inhibition) at suboptimal doses, however, when combined with NTZ, reach an inhibition of α-SMA in the order of 60 to 70%. Tizoxanide, the active metabolite of NTZ, was also evaluated in combination with the statins that revealed the best synergism with NTZ, namely Pitavastatin, Simvastatin and Fluvastatin. As observed with NTZ, the TZ metabolite also synergized with these 3 statins (an example with Fluvastatin is shown in FIG. 9).

To confirm the synergistic anti-fibrotic properties of NTZ/statin combinations in a preclinical model of liver fibrosis, a chronic study was conducted in the $CCl_4$ rat model. Indeed, Carbon tetrachloride ($CCl_4$) is a hepatotoxin widely used for the study of various degrees of liver damage in rodents (Constandinou et al, 2005). In many aspects, it mirrors the pattern of human disease associated with toxic damage and this model is a well recognized model of chemically-induced liver fibrosis. Accordingly, significant inductions of hepatic collagen content (FIG. 11A) and liver fibrosis area (FIG. 11B) were observed after 7 wks of $CCl_4$ exposure compared to the animals exposed to the olive oil. A synergistic effect (determined by EOHSA model, Borisy 2003) on fibrosis area (FIG. 11) was observed in the liver of $CCl_4$-treated rats that were administered both Nitazoxanide 30 mg/kg/day and Atorvastatin 30 mg/kg/day as compared to rats receiving either treatment only. The reduction in fibrosis outcome was twofold with the combination, as compared to the single agents used at the same doses as in the combination. In addition, to their antifibrotic properties, it was found that a combination of NTZ at 30 mg/kg/day with Simvastatin at 10 mg/kg/day synergized to prevent the occurrence of altered levels of circulating bile acids in a model of CCl4-induced liver injury (FIG. 10). In conclusion, the applicant has discovered unexpected anticholestatic and antifibrotic activities for a combination of a compound of Formula (I) statins. These results suggest that a combination of a compound of Formula (I) with a statin can be synergistic and can provide therapeutic benefits in multiple types of cholestatic and fibrotic diseases.

REFERENCES

Borisy, A. A., P. J. Elliott, et al. (2003). "Systematic discovery of multicomponent therapeutics." *Prod Natl Acad Sci USA* 100(13): 7977-7982Broekhuysen, J., A. Stockis, et al. (2000), "Nitazoxanide: pharmacokinetics and metabolism in man." *Int J Clin Pharmacol Ther* 38(8): 387-394.

Chong, L. W., Y. C. Hsu, et al. (2015), "Fluvastatin attenuates hepatic steatosis-induced fibrogenesis in rats through inhibiting paracrine effect of heoatocyte on hepatic stellate cells." *BMC Gastroenterol* 15: 22.

Constandinou, C., N. Henderson, et al. (2005). "Modeling liver fibrosis in rodents." *Methods Mol Med* 117: 237-250.de Carvalho, L P. S., C. M. Darby, et al. (2011). "Nitazoxanide disrupts membrane potential and intrabacterial pH homeostasis of *Mycobacterium tuberculosis*." *ACS Med. Chem. Lett.* 2(Copyright (C) 2015 American Chemical Society (ACS). All Rights Reserved.): 849-854.

Di Santo, N. and J. Ehrisman (2014). "A functional perspective of nitazoxanide as a potential anticancer drug." *Mutat. Res., Fundam, Mol Mech. Mutagen.* 768(Copyright (C) 2015 American Chemical Society (ACS). All Rights Reserved.): 16-21.

Dubreuil, L., I. Houcke, et al. (1996). "In vitro evaluation of activities of nitazoxanide and tizoxanide against anaerobes and aerobic organisms." *Antimicrob. Agents Chemother.* 40(Copyright (C) 2015 American Chemical Society (ACS). All Rights Reserved.): 2266-2270.

Finegold, S. M., D. Molitoris, et al. 2009). "Study of the in vitro activities of rifaxirnin and comparator agents against 536 anaerobic intestinal bacteria from the perspective of potential utility in pathology involving bowel flora." *Antimicrob. Agents Chemother,* 53(Copyright (C) 2015 American Chemical Society (ACS). All Rights Reserved.): 281-286.

Fox, L M. and L. D. Saravolatz (2005). "Nitazoxanide: a new thiazolide antiparasitic agent." *Clin. Infect. Dis.* 40(Copyright (C) 2015 American Chemical Society (ACS). All Rights Reserved.): 1173-1180.

Hemphill, A., J. Mueller, et al. (2006). "Nitazoxanide, a broad-spectrum thiazolide anti-infective agent for the treatment of gastrointestinal infections." *Expert Opin. Pharmacother.* 7(Copyright (C) 2015 American Chemical Society (ACS). All Rights Reserved.): 953-964.

Hoffman, P. S., G. Sisson, et al, (2007). "Antiparasitic drug nitazoxanide inhibits the pyruvate oxidoreductases of *Helicobacter pylori*, selected anaerobic bacteria and parasites, and *Campylobacter jejuni.*" *Antimicrob. Agents Chemother.* 51(Copyright (C) 2015 American Chemical Society (ACS). All Rights Reserved.): 868-876.

Ji, H., H. Tang, et al. (2014). "Rho/Rock cross-talks with transforming growth factor-beta/Smad pathway participates in lung fibroblast-myofibroblast differentiation." *Biomed Rep* 2(6): 787-792.

Kavalipati, N., J, Shah, et al. (2015). "Pleiotropic effects of statins." *Indian J Endocrinol Metab* 19(5): 554-562.

Kendall, R. T. and C. A. Feghali-Bostwick (2014). "Fibroblasts in fibrosis: novel roles and mediators," *Front Pharmacol* 5: 123.

Leask, A. (2007). "TGFbeta, cardiac fibroblasts, and the fibrotic response." *Cardiovasc Res* 74(2): 207-212.

Leask, A. and D. J. Abraham (2004). "TGF-beta signaling and the fibrotic response." *FASEB J* 18(7): 816-827.

Marrone, G., R. Maeso-Diaz, et al. (2015). "KLF2 exerts antifibrotic and vasoprotective effects in cirrhotic rat livers: behind the molecular mechanisms of statins," *Gut* 64(9): 1434-1443.

McFarlane, S I., R. Muniyappa, et al, (2002). "Clinical review 145: Pleiotropic effects of statins; lipid reduction and beyond." *J Clin Endocrinol Metab* 87(4): 1451-1458.

McKenney, J. M. (2003). "Pharmacologic characteristics of statins." *Clin Cardiol* 26(4 Suppl 3): III32-38.

Megraudd, F., A. Occhialini, et al. (1998). "Nitazoxanide, a potential drug for eradication of *Helicobacter pylori* with no cross-resistance to metronidazole." *Antimicrob. Agents Chemother.* 42(Copyright (C) 2015 American Chemical Society (ACS). All Rights Reserved): 2836-2840.

Miyaki, T., S. Noliri, et al. (2011). "Pitavastatin inhibits hepatic steatosis and fibrosis in non-alcoholic steatohepatitis model rats." *Hepatol Res* 41(4): 375-385.

Pankuch, G. A. and P. C. Appelbaum (2006). "Activities of tizoxanide and nitazoxanide compared to those of five other thiazolides and three other agents against anaerobic species." *Antimicrob. Agents Chemother.* 50(Copyright (C) 2015 American Chemical Society (ACS). All Rights Reserved.): 1112-1117.

Rombouts, K., E. Kisanga, et al. (2003). "Effect of HMG-CoA reductase inhibitors on proliferation and protein synthesis by rat hepatic stellate cells." *J Hepatol* 38(5): 564-572.

Rosenbloom, J., F. A. Mendoza, et al. (2013). "Strategies for anti-fibrotic therapies." *Biochim Biophys Acta* 1832(7): 1088-1103.

Rossignol, J.-F. (2014). "Nitazoxanide: A first-in-class broad-spectrum antiviral agent" *Antiviral Res.* 110(Copyright (C) 2015 American Chemical Society (ACS). All Rights Reserved.): 94-103.

Rossignol, J. F. and R. Cavier (1975). 2-Benzamido-5-nitrothiazoles, S. P. R. L. Phavic, Belg. 11 pp.

Rossignol, J. F. and H. Maisonneuve (1984). "Nitazoxanide in the treatment of Taenia saginata and *Hymenoiepis nana* infections." *Am J Trop Med Hyg* 33(Copyright (C) 2015 U.S. National Library of Medicine.): 511-512.

Wang, C. Y. P. Y. Liu, et al. (2008). "Pleiotropic effects of statin therapy: molecular mechanisms and clinical results." *Trends Mol Med* 14(1): 37-44.

Wang, W., C. Zhao, et al. (2013). "Simvastatin ameliorates liver fibrosis via mediating nitric oxide synthase in rats with non-alcoholic steatohepatitis-related liver fibrosis." *PLoS One* 8(10): e76538.

Watts, K. L., E. M. Sampson, et al. (2005). "Simvastatin inhibits growth factor expression and modulates profibrogenic markers in lung fibroblasts." *Am J Respir Cell Mol Biol* 32(4): 290-300.

Yedaneh, B., E. Wiechec, et al. (2014). "Targeting the mevalonate cascade as a new therapeutic approach in heart disease, cancer and pulmonary disease." *Pharmacol Ther* 143(1): 87-110.

Zhou, Q. and J. K. Liao (2009), "Statins and cardiovascular diseases: from cholesterol lowering to pleiotropy." *Curr Pharm Des* 15(5): 467-478.

Zhu, B., A. Q. Ma, et al. (2013). "Atorvastatin attenuates bleomycin-induced pulmonary fibrosis via suppressing iNOS expression and the CTGF (CCN2)/ERK signaling pathway." *Int J Mol Sci* 14(12): 24476-24491.

The invention claimed is:

1. A method of treating liver fibrosis comprising administering a therapeutically effective amount of a pharmaceutical composition to a subject in need thereof, wherein the pharmaceutical composition consists essentially of (i) nitazoxanide (NTZ) or tizoxanide (TZ), or a pharmaceutically acceptable salt of NTZ or TZ; and (ii) Atorvastatin.

2. The method according to claim 1, wherein the liver fibrosis is selected from the group consisting of non-alcoholic steatohepatitis (NASH), alcohol-induced liver fibrosis, drug-induced liver fibrosis, and liver cirrhosis.

3. A method of treating liver fibrosis, the method consisting essentially of administrating simultaneously, sequentially or separately a therapeutically effective amount of:
   (i) Nitazoxanide (NTZ) and
   (ii) Atorvastatin,
   to a subject in need thereof.

4. The method of claim 3, wherein the liver fibrosis is selected from the group consisting of non-alcoholic steatohepatitis (NASH), alcohol-induced liver fibrosis, drug-induced liver fibrosis, and liver cirrhosis.

5. The method of according to claim 1, wherein the pharmaceutical composition consists essentially of (i) NTZ; and (ii) Atorvastatin.

6. The method according to claim 5, wherein the liver fibrosis is selected from the group consisting of non-alcoholic steatohepatitis (NASH), alcohol-induced liver fibrosis, drug-induced liver fibrosis, and liver cirrhosis.

* * * * *